United States Patent
Peet et al.

(10) Patent No.: US 6,265,381 B1
(45) Date of Patent: Jul. 24, 2001

(54) ORALLY-ACTIVE ELASTASE INHIBITORS

(75) Inventors: Norton P. Peet, Cincinnati; Michael R. Angelastro, Mason; Joseph P. Burkhart, West Chester, all of OH (US)

(73) Assignee: Merrell Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 09/491,814

(22) Filed: Jan. 28, 2000

Related U.S. Application Data

(63) Continuation of application No. 08/438,289, filed on May 10, 1995, now abandoned, which is a continuation-in-part of application No. 08/323,418, filed on Oct. 13, 1994, now Pat. No. 5,478,811, which is a continuation of application No. 08/127,966, filed on Sep. 28, 1993, now abandoned, which is a continuation of application No. 07/918,561, filed on Jul. 29, 1992, now abandoned, which is a continuation-in-part of application No. 07/748,607, filed on Aug. 22, 1991, now abandoned.

(51) Int. Cl.[7] .................................................... A61K 38/00

(52) U.S. Cl. ............................. 514/18; 530/330; 530/331

(58) Field of Search .............................. 514/18; 530/330, 530/331

(56) References Cited

U.S. PATENT DOCUMENTS

| | | |
|---|---|---|
| 4,277,395 | 7/1981 | Bey et al. . |
| 4,518,528 | 5/1985 | Rasnick . |
| 4,623,639 | 11/1986 | Hassall . |
| 4,629,724 | 12/1986 | Ryone et al. . |
| 4,636,489 | 1/1987 | Seemuller et al. . |
| 4,643,991 | 2/1987 | Digenis et al. . |
| 4,855,303 | 8/1989 | Hoover . |
| 4,873,221 | 10/1989 | Trainor et al. . |
| 4,880,780 | 11/1989 | Trainor et al. . |
| 4,910,190 | 3/1990 | Bergeson et al. . |
| 4,935,405 | 6/1990 | Hoover et al. . |
| 5,055,450 | 10/1991 | Edwards et al. . |
| 5,114,927 | 5/1992 | Schirlin . |
| 5,162,307 | 11/1992 | Digenis et al. . |
| 5,221,665 | 6/1993 | Skiles et al. . |
| 5,478,811 | 12/1995 | Peet et al. . |
| 5,496,927 | 3/1996 | Kolb et al. . |
| 5,510,333 | 4/1996 | Angelastro et al. . |

FOREIGN PATENT DOCUMENTS

| | | |
|---|---|---|
| 0318318 | 11/1988 | (EP) . |
| 0369391 | 5/1990 | (EP) . |
| 0410411 | 1/1991 | (EP) . |
| 0494071 | 1/1991 | (EP) . |
| 0529568 A1 | * 3/1993 | (EP) . |
| 9115487 | 3/1990 | (WO) . |
| 9113904 | 3/1991 | (WO) . |
| 9215605 | 9/1992 | (WO) . |

OTHER PUBLICATIONS

Imperiali et al., "Inhibition of Serine Proteases by Peptidyl Fluoromethyl Ketones," Biochemistry vol. 21, pp. 3760–3767 (1986).

Skiles et al., Inhibition of Human Leukocyte Elastase (HLE) by N–Substituted Peptidyl Trifluoromethyl Ketones, J. of Medicinal Chemistry, vol. 35, No. 4, pp. 641–662 (1992).

Repine et al., "Renin Inhibitors Containing Esters at the P2–Position. Oral Activity in a Derivative of Methyl Aminomalonate," J. Med. Chem. 34, pp. 1935–1943, (1991).

Ueda et al., "The synthesis of arginylfluoroalkanes, their inhibition of trypsin and blood–coagulation serine proteinases and their anticoagulant activity," Biochem. J. 265, pp. 539–545, (1990).

Sham, H.L. et al., "Highly potent and specific inhibitors of human renin," FEBS Letters, vol. 220, No. 2, pp. 299–301, (1987).

Powers, J.C., Eleventh American Peptide Syposium, Abstracts, The Salk Institute and U. of CA, San Diego (1989).

Travis, J. et al., "Potential Problems in Designing Elastase Inhibitors for Therapy," Am Rev Respir Dis, Pulmonary Perspective, vol. 143 pp. 1412–1415 1991.

Petrillo, E.W., et al., Chapter 6. Antihypertensive Agents, Section II. Cardiovascular and Pulmonary Agents, Annual Reports in Medicinal Chemistry, 25, 1989, Academic Press, Inc., D.W. Robertson Editor.

Chemical Abstract vol. 111, No. 21, Nov. 20, 1989, Galzigna et al 190131z.

Chemical Abstract Vo. 111, No. 9, Aug. 28, 1989, Lafuma et al 70314q.

Powers et al, Chemical Abstracts, vol. 108:33954r, 1988, "Mechanism–based inhibitors of human leukocyte elastase".

Steinmeyer et al, "Influence of Some Natural and Semisynthetic Agents on Elastase and Cathepsin G from Polymorphonuclear Granulocytes," Arzneim–Forsch/Drug Res. 41(I), Nr.1 (1991), pp. 77–80.

McWherter et al, "Novel Inhibitors of Human Leukocyte Elastase and Cathepsin G, Sequence Variants of Squash Seet Protease Inhibitor with Altered Protease Selectivity," Biochemistry, 1989, 28, 5708–5713.

Reilly et al, "The Degradation of Human Lung Elastin by Neutrophil Proteinases," Biochimica et Biophysica Acta, 621 (1980) pp. 147–157.

(List continued on next page.)

*Primary Examiner*—Dwayne C. Jones
*Assistant Examiner*—C. Delacroix-Muirheid
(74) *Attorney, Agent, or Firm*—Balaram Gupta

(57) ABSTRACT

This invention relates to novel morpholinourea and related derivatives of pentafluoroethyl peptides which are orally active elastase inhibitors. These compounds are useful in the treatment of various inflammatory diseases and emphysema.

8 Claims, No Drawings

OTHER PUBLICATIONS

Nakajima et al, "Mapping the Extended Substrate Binding Site of Cathepsin G and Human Leukocyte Elastase," The Journal of Biological Chemistry vol. 254, No. 10, pp. 4027–4032, 1979.

Rice et al, "Regulation of Proteolysis at the Neutrophil–Substrate Interface by Secretory Leukoprotease Inhibitor," Science, vol. 249, pp. 178–181, Jul. 13, 1990.

Travis, "Structure, Function, and control of Neutrophil Proteinases," Jun. 24, 1988, The American Journal of Medicine, vol. 84 (Suppl 6A) pp. 37–42.

Peet et al, "Synthesis of Peptidyl Fluoromethyl Ketones and Peptidyl α–Keto Esters as Inhibitors of Procine Pancreatic Elastase, Human Neutrophil Elastase, and Rat and Human Neutrophil Cathepsin G," J. Med Chem, 1990, 33, pp. 394–407.

Doherty et al, "Novel Inhibitors of Polymorphonuclear Neutrophil (PMN) Elastase and Cathepsin G: Evaluation in vitro of their potential for the Treatment of inflammatory connective tissue damage," Int. J. Immunopharmac, vol. 12, No. 7, pp. 787–795, 1990.

Mehdi et al, "The inhibition of human Neutrophil elastase and cathepsin G by Peptidyl 1,2–dicarbonyl derivatives," Biochemical and Biophysical Research Communications, vol. 166, No. 2, 1990, pp. 595–600.

Shah et al, "Orally Active β–Lactam Inhibitors of Human Leukocyte Elastase–1." J. Med Chem, 35, pp. 3745–3754 (1992).

Snider, "Experimental Studies on Emphysema and Chronic Bronchial Injury," Eur. J. Respir Dis (1986) 69 (Suppl. 146) pp. 17–35.

Malech et al, "Current Concepts: Immunology Neutrophils in Human Diseases," Medical Intelligence– vol. 317. No. 11, No month or year given.

Fletcher et al, "A comparison of β1—Proteinase Inhibitor Methoxysuccinyl–ala–ala–pro–val–chloromethylketone and Specific–Lactam Inhibitors in a accute Model of Human Polymorphonuclear Leukocyte Elastase–induced Lung Hemorrhage in the hamster," Am.Rev.Respir Dis. 1990; 141:672–677.

Hassall et al, "A new class of inhibitors of human leukocyte elastase," FEBS 2444, vol. 183, No. 2, Apr. 1985.

Angelastro et al, "Inhibition of Human Neutrophil Elastase with Peptidyl Electrophilic Ketones," J. of Med. Chem., 37, pp. 4538–4553 (1994).

Burkhart et al, "Inhibition of Human Neutrophil Elastase," J. Med. Chem. 1995, 38, pp. 223–233.

Angelastro et al, "An Efficient Synthesis of Novel α–Diketone and α–Keto Ester Derivatives of N–Protected Amino Acids and Peptides," J. Org. Chem. 54, pp. 3913–3916, (1989).

Burkhart, et al., "A Novel Methlod for the Preparation of Peptidyl α–Keto Esters," Tetrahedron Letters, vol. 31, No. 10, pp. 1385–1388 (1990).

Angelastro et al., "Efficient Preparation of Peptidyl Pentafluoroethyl Ketones," Tetrahedron Letters, vol. 33, No. 23, pp. 3265–3268 (1992).

Mehdi, "Review," Bioorganic Chemistry, 21, pp. 249–259 (1993).

Angelastro et al, "Janus Compounds: Dual Inhibitors of Proteinase," Bioorganic & Med. Chem. Letters, vol. 3, No. 4, pp. 525–530 (1993).

Angelastro et al, Bioorganic & Medicinal Chemistry Letters, vol. 2, No. 10, pp. 1235–1238 (1992).

J. Med. Chem. 33, pp. 11–13 (1990) Communications to the Editor.

Janusz, M. et al., J. Immunol. (1991), vol. 146, pp.3922–3928.

Janusz, M. et al, J. Pharmacol. Exp. Ther., (1995), vol. 275, pp. 1233–1238.

Durham, S. et al, J. Pharmacol. Exp. Ther., (1994), vol. 270, pp. 185–191.

* cited by examiner

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO: 1:

Xaa Xaa Xaa Xaa
1

(2) INFORMATION FOR SEQ ID NO: 2:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 1
      (D) OTHER INFORMATION: /note= "morpholino carbonyl
         protected"

(ix) FEATURE:
      (A) NAME/KEY: Modified-site
      (B) LOCATION: 4
      (D) OTHER INFORMATION: /note= "terminal OH is replaced by
         a perfluoroethyl group"

(xi) SEQUENCE DESCRIPTION: SEQ ID NO: 2:

Ala Ala Pro Val
1

(2) INFORMATION FOR SEQ ID NO: 3:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note=
           "4(morpholinocarbonyl)benzoyl protected"

(ix) FEATURE:
        (A) NAME/KEY: Modified-site
        (B) LOCATION: 4
        (D) OTHER INFORMATION: /note= "terminal OH group replaced
           by a perfluoroethyl group"

(xi) SEQUENCE DESCRIPTION: SEQ ID NO: 3:

Ala Ala Pro Val
1

(2) INFORMATION FOR SEQ ID NO: 4:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 4:

Xaa Xaa Xaa Xaa
1

(2) INFORMATION FOR SEQ ID NO: 5:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 5:

Xaa Xaa Xaa Xaa

ORALLY-ACTIVE ELASTASE INHIBITORS

This is a continuation of application Ser. No. 08/438,289 filed May 10, 1995, now abandoned; which is a continuation-in-part of application Ser. No. 08/323,418, filed Oct. 13, 1994, now U.S. Pat. No. 5,478,811, issued Dec. 26, 1995; which is a continuation of application Ser. No. 08/127,966, filed Sep. 28, 1993, now abandoned; which is a continuation of application Ser. No. 07/918,561, filed Jul. 29, 1992, now abandoned; which is a continuation-in-part of application Ser. No. 07/748,607, filed Aug. 22, 1991 now abandoned.

This invention relates to orally-active elastase inhibitors useful for a variety of physiological end-use applications.

In its broad aspects, this invention relates to analogs of peptidase substrates in which the carboxy terminal carboxyl group has been replaced by a pentafluoroethylcarbonyl (—C(O)C$_2$F$_5$)group and in which the amino terminal amino acid is protected by various heterocycle-containing groups such as a 4-morpholinecarbonyl group. These elastase inhibitors exert valuable pharmacological activities and therefore have useful physiological consequences in a variety of disease states.

In its more specific aspects, this invention relates to pentafluoroethylcarbonyl analogs of certain elastase substrates which have various heterocyclic containing protecting groups which are useful in inhibiting elastase, the inhibition of which will have useful physiological consequences in a variety of disease states.

The contemplated elastase inhibitors are selected from the generic formulae

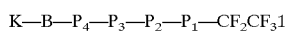  (SEQ. ID NO. 1)

wherein

P$_1$ is Ala, bAla, Leu, Ile, Val, Nva, bVal, Met, Nle, or an N-methyl derivative;

P$_2$ is Ala, bAla, Leu, Ile, Val, Nva, bVal, Met, Nle, Gly, Phe, Tyr, Trp, or Nal(1) where the nitrogen of the alpha-amino group can be substituted with an R group where R is a (C$_{1-6}$)alkyl, (C$_{3-12}$)cycloalkyl, (C$_{3-12}$)cycloalkyl(C$_{1-6}$)alkyl, (C$_{4-11}$)bicycloalkyl, (C$_{4-11}$)bicycloalkyl(C$_{1-6}$)alkyl, (C$_{6-10}$)aryl, (C$_{6-10}$)aryl(C$_{1-6}$)alkyl, (C$_{3-7}$)heterocycloalkyl, (C$_{3-7}$)heterocycloalkyl(C$_{1-6}$)alkyl, (C$_{5-9}$)heteroaryl, (C$_{5-9}$)heteroaryl(C$_{1-6}$)alkyl, fused (C$_{6-10}$)aryl-(C$_{3-12}$)cycloalkyl, fused (C$_{6-10}$)aryl(C$_{3-12}$)cyclo-alkyl(C$_{1-6}$)alkyl, fused (C$_{5-9}$)heteroaryl(C$_{3-12}$)cycloalkyl, or fused (C$_{5-9}$)heteroaryl(C$_{3-12}$)cycloalkyl-(C$_{1-6}$)alkyl, or P$_2$ is Pro, 1,2,3,4-tetrahydro-3-isoquinoline carboxylic acid (Tic), thiazolidine-4-carboxylic acid (Tca), or Ind;

P$_3$ is Ala, bAla, Leu, Ile, Val, Nva, bVal, Met, or Nle or an N-methyl derivative, Pro, Ind, Tic or Tca, Lys or Orn each substituted on its omega amino group with a morpholino-B-group;

P$_4$ is Ala, bAla, Leu, Ile, Val, Nva, bVal, Met, or Nle or an N-methyl derivative or a bond;

B is a group of the formulae

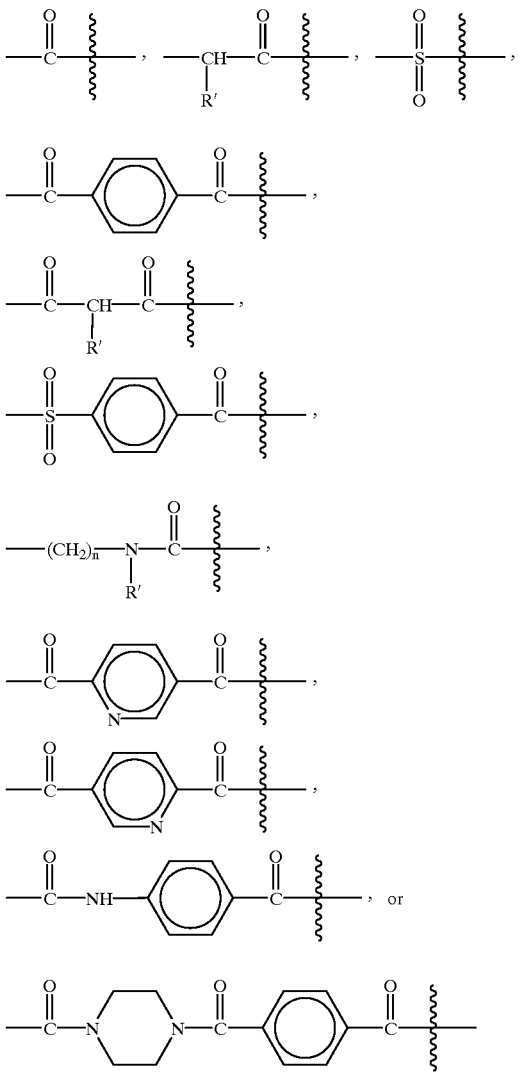

(the wavy line  being that attachment to the rest of the molecule, e.g., not to X)

R' is a hydrogen or a C$_{1-6}$ branched or straight chain alkyl group;

n is zero or the integers 1 or 2;

K is

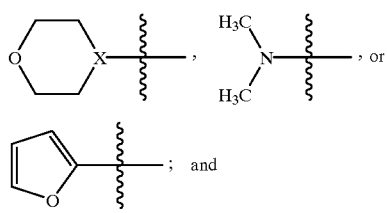

X is N or CH;

or a hydrate, isostere, or pharmaceutically acceptable salt thereof;

Isosteres of the compounds of formula 1 include those wherein (a) one or more of the α-amino residues of the $P_1$–$P_4$ substituents are in its unnatural configuration (when there is a natural configuration) or (b) when the normal peptidic amide linkage is modified, such as for example, to form —$CH_2NH$— (reduced), —$COCH_2$— (keto), —CH(OH)$CH_2$— (hydroxy), —CH($NH_2$)$CH_2$— (amino), —$CH_2CH_2$— (hydrocarbon), —CH=CH— (alkene). Preferably a compound of the invention should not be in an isosteric form; particularly it is preferred that there be no modified peptidic amide group, but if there is, it is preferable to keep the isosteric modifications to a minimum. Of course, it is also understood that in those instances wherein the carbonyl moiety of $P_1$ is in its reduced form, then such compounds are not hydrates.

As used herein the term "($C_{1-6}$)alkyl" means a straight or branched alkyl group of from 1 to 6 carbon atoms, such as, methyl, ethyl, n-propyl, isopropyl, n-butyl, tert-butyl, n-pentyl, sec-pentyl, iso-pentyl, and n-hexyl. The term "($C_{3-12}$)cycloalkyl" means a cyclic alkyl group consisting of a 3 to 8 member ring which can be substituted by a lower alkyl group, for example, cyclopropyl, cyclobutyl, cyclopentyl, cyclohexyl, 4-methylcyclohexyl, 4-ethylcyclohexyl, cycloheptyl, and cyclooctyl. The term "($C_{3-12}$)cycloalkyl($C_{1-6}$)alkyl" means a ($C_{1-6}$)alkyl group substituted by a ($C_{3-12}$)cycloalkyl group, such as a cyclohexylmethyl or cyclopentylethyl group. The term "($C_{4-11}$)bicycloalkyl" means an alkyl group containing one pair of bridgehead carbon atoms, such as 2-bicyclo[1.1.0]-butyl, 2-bicyclo[2.2.1]hexyl, and 1-bicyclo[2.2.2]octane. The term "($C_{4-11}$)bicycloalkyl($C_{1-6}$)alkyl" means a ($C_{1-6}$)alkyl substituted by a ($C_{4-11}$)bicycloalkyl, such as 2-bicyclohexlymethyl. The term "($C_{6-10}$)aryl" means a cyclic, aromatic assemblage of conjugated carbon atoms, for example, phenyl, 1-naphthyl, and 2-naphthyl. The term "($C_{6-10}$)aryl($C_{1-6}$)alkyl" means a ($C_{1-6}$)alkyl substituted by a ($C_{6-10}$)aryl, such as benzyl, phenethyl, and 1-naphthylmethyl. The term "($C_{3-7}$)heterocycloalkyl" means a nonaromatic, carbon containing cyclic group which contains from 1 to 3 heteroatoms selected from oxygen, nitrogen and sulfur, such as morpholinyl and piperidinyl. The term "($C_{3-7}$)heterocycloalkyl($C_{1-6}$)alkyl" means a ($C_{1-6}$)alkyl group substituted by a ($C_{3-7}$)heterocycloalkyl group, for example, morpholinomethyl. The term "($C_{5-9}$)heteroaryl" means a cyclic or bicyclic, aromatic assemblage of conjugated carbon atoms and from 1 to 3 nitrogen, oxygen, and sulfur atoms, for example, pyridinyl, 2-quinoxalinyl, and quinolinyl. The term "($C_{5-9}$)heteroaryl($C_{1-6}$)alkyl" means ($C_{1-6}$)alkyl group substituted by a ($C_{5-9}$)heteroaryl group, such as, 3-quinolinylmethyl. The term "fused ($C_{6-10}$)aryl($C_{3-12}$)cycloalkyl" means a "($C_{3-12}$)cycloalkyl" group which has one or more sides shared with a "($C_{6-10}$)aryl" group and can, for example, include groups derived by the fusion of benzene and cyclopentane, that is 2-indanyl. The term "fused ($C_{6-10}$)aryl ($C_{3-12}$)cycloalkyl($C_{1-6}$)alkyl" means a ($C_{1-6}$)alkyl substituted by a fused ($C_{6-10}$)aryl($C_{3-12}$)cycloalkyl group. The term "fused ($C_{5-9}$)heteroaryl($C_{3-8}$)cycloalkyl" means a ($C_{5-9}$)heteroaryl group which has one or more sides shared with a ($C_{3-8}$)cycloalkyl group and can, for example, include groups derived by the fusion of cyclohexane and pyridine, that is tetrahydroquinoline. Finally the term "fused ($C_{5-9}$)heteroaryl($C_{3-8}$)cycloalkyl($C_{1-6}$)alkyl" means a ($C_{1-6}$)alkyl substituted by a fused ($C_{5-9}$)heteroaryl($C_{3-8}$)cycloalkyl group.

Unless otherwise stated, the α-amino acids of these peptidase substrate analogs are preferably in their L-configuration; however, applicants contemplate that the amino acids of the formula 1 compounds can be of either the D- or L-configurations or can be mixtures of the D- and L-isomers, including the racemic mixture. Also, the carbon adjacent to the carboxy terminal —C(=O)$CF_2CF_3$ moiety can also be the D- or the L-optical isomer and can also be a mixture of such isomers. The recognized abbreviations for the α-amino acids are set forth in Table I.

TABLE I

| AMINO ACID | SYMBOL |
| --- | --- |
| Alanine | Ala |
| Glycine | Gly |
| Isoleucine | Ile |
| Leucine | Leu |
| Lysine | Lys |
| Phenylalanine | Phe |
| Proline | Pro |
| Tryptophan | Trp |
| Tyrosine | Tyr |
| Valine | Val |
| Norvaline | Nva |
| Norleucine | Nle |
| 1-Naphthylalanine | Nal (1) |
| 2-Indolinecarboxylic acid | Ind |
| Sarcosine | Sar |
| beta-Alanine | bAla |
| beta-Valine | bVal |
| Methionine | Met |
| 1,2,3,4-Tetrahydro-3-isoquinoline carboxylic acid | Tic |
| Thiazolidine-4-carboxylic acid | Tca |
| Ornithine | Orn |

Some of the preferred compounds of this invention are also morpholino urea derivatives by virtue of the fact that the amino terminal amino group of the peptide chain is protected by a 4-morpholinecarbonyl group. The 4-morpholinecarbonyl protecting group of the formula

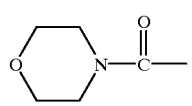

is abbreviated throughout as MC. Other preferred compounds of this invention are 4-morpholinecarbonylbenzoyl, abbreviated throughout as MCBz, derivatives wherein the morpholine-B group is of the formula

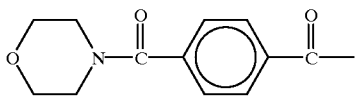

Yet other preferred copounds of this invention are 4-morpholine sulfonylbenzoyl derivatives wherein the morpholine-B group is of the formula

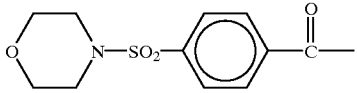

Still other preferred compounds of this invention are 2-(N-morpholinocarbonyl)-3-methyl-butanoyl derivatives wherein the morpholine-B group is of the formula

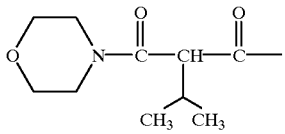

Of the compounds of formula 1 applicants also prefer those compounds wherein $P_1$ is norvaline or valine. Also preferred are those formula 1 compounds wherein $P_2$ is a proline or glycine; wherein $P_3$ is isoleucine, valine, or alanine; and wherein $P_4$ is alanine or is a bond. Other preferred compounds of formula 1 are those wherein alpha amino group of the $P_2$ group is substituted by an R group, especially those wherein the R group is a methyl group or a 2-indanyl group. Specifically preferred compounds of formula 1 are:

| | |
|---|---|
| MC-Ala-Ala-Pro-Val-$C_2F_5$; | SEQ. ID 2 |
| MC-Val-Pro-Val-$C_2F_5$; | |
| MCBZ-Ala-Ala-Pro-Val-$C_2F_5$; | SEQ. ID 3 |
| MCBZ-Val-Pro-Val-$C_2F_5$; | |

N-[(Dimethylamino)carbonyl]-L-valyl-N-[3,3,4,4,4-pentafluoro-1-(1-methylethyl)-2-oxobutyl]-L-prolinamide;

N-[(Tetrahydro-2H-pyran-4-yl)carbonyl]-L-valyl-N-[3,3,4,4,4-pentafluoro-1-methylethyl)-2-oxobutyl]-L-prolinamide;

N-(2-Furoyl)-L-valyl-N-[3,3,4,4,4-pentafluoro-1-(1-methylethyl)-2-oxobutyl]-L-prolinamide;

N-[2-(4-Morpholinyl)ethanoyl]-L-valyl-N-[3,3,4,4,4-pentafluoro-1-(1-methylethyl)-2-oxobutyl]-L-prolinamide, Hydrochloride Salt;

N-[3-(4-Morpholinyl)-1,3-dioxopropyl]-L-valyl-N-[3,3,4,4,4-pentafluoro-1-(1-methylethyl)-2-oxobutyl]-L-prolinamide;

N-[3-Methyl-2-(4-morpholinylcarbonyl)-1-oxobutyl]-L-valyl-N-[3,3,4,4,4-pentafluoro-1-(1-methylethyl)-2-oxobutyl]-L-prolinamide;

N-[[6-(4-Morpholinylcarbonyl)pyrid-3-yl]carbonyl]-L-valyl-N-[3,3,4,4,4-pentafluoro-1-(1-methylethyl)-2-oxobutyl]-L-prolinamide;

N-[4-(4-Morpholinylsulfonyl)benzoyl]-L-valyl-N-[3,3,4,4,4-pentafluoro-1-(1-methylethyl)-2-oxobutyl]-L-prolinamide;

N-[4-[(4-Morpholinylcarbonyl)amino]benzoyl]-L-valyl-N-[3,3,4,4,4-pentafluoro-1-(1-methylethyl)-2-oxobutyl]-L-prolinamide;

N-[4-[[Methyl[2-(4-morpholinyl)ethyl]amino]carbonyl]-benzoyl]-L-valyl-N-[3,3,4,4,4-pentafluoro-1-(1-methylethyl)-2-oxobutyl]-L-prolinamide;

N-[4-[[4-(4-Morpholinylcarbonyl)-1-piperazinyl]carbonyl]benzoyl]-L-valyl-N-[3,3,4,4,4-pentafluoro-1-(1-methylethyl)-2-oxobutyl]-L-prolinamide.

Human leukocyte elastase is released by polymorphonuclear leukocytes at sites of inflammation and thus is a contributing cause for a number of disease states. Thus the peptidase substrates of formula 1 have an anti-inflammatory effect useful in the treatment of gout, rheumatoid arthritis and other inflammatory diseases, such as adult respiratory distress syndrome, septicemia, and disseminated intravascular coagulation, cystic fibrosis, chronic bronchitis, inflammatory bowel disease, and in the treatment of emphysema. In their end-use application the enzyme inhibitory properties of the compounds of formula 1 are readily ascertained by standard biochemical techniques well known in the art. Potential dose range for their end-use application will of course depend upon the nature and severity of the disease state as determined by the attending diagnostician with the range of 0.01 to 200 mg/kg body weight per day being useful for the aforementioned disease states with 0.1 mg to 50 mg/kg per day being preferred.

Human elastase is assayed in vitro using chromophoric peptides, succinylalanylalanylalanyl-p-nitroanilide, methoxysuccinylalanylalanylprolylvalyl-p-nitroanilide, and others, all of which are available commercially. The assay buffer, pH 8.0, and assay techniques are similar to those described by R. Lottenberg, et al., *Biochimica et Biophysica Acta*, 742, pp. 539–557 (1983). Enzyme is purified from human sputum, although recently it has become commercially available. Kinetic characterization of immediate inhibitors is by means of the Dixon plot, whereas the characterization of slow- and/or tight-binding inhibitors used data analysis techniques reviewed by Williams and Morrison. The synthesis and analytical use of a highly sensitive and convenient substrate of elastase is described in J. Bieth, B. Spiess and C. G. Wermuth, *Biochemical Medicine*, 11 (1974) 350–375. Table 2 summarizes the ability of selected compounds of this invention and a compound of the prior art to inhibit elastase. Table 2A summarizes the ability of other selected compounds of this invention and a compound of the prior art to inhibit elastase. Table 3 summarizes the oral activity of various compounds when evaluated in the elastase-induced hemmorrhage model in hamster or the elastase-induced hemmorrhage model in rats. The methodologies for each model are well known in the art and are disclosed in M. Angelastro et al., *J. Med. Chem.* 37, 4538–4553 (1994), said reference being incorporated by reference as if fully set forth.

TABLE 2

(R—ValProValC₂F₅)

| MDL # | R | $K_i$(nM)* |
|---|---|---|
| 101,146 | 4-(morpholine-4-carbonyl)benzoyl | 20 |
| 102,823 | tetrahydropyran-4-carbonyl | 60 |
| 100,948A | morpholinoacetyl · HCl | 60 |
| 102,111 | 1,3-oxazinane-3-carbonyl | 170 |
| 101,773 | N,N-dimethylcarbamoyl | 261 |
| 101,788 | 4-(morpholine-4-sulfonyl)benzoyl | 2.36 |
| 100,050 | 2-(morpholine-4-carbonyl)-3-methylbutanoyl | 44 |
| — | 2-furoyl (with gem-dimethyl) | 190 |

TABLE 2-continued
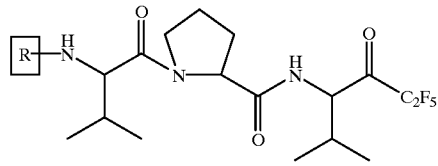
( R — ValProValC₂F₅ )
| MDL # | R | $K_i$(nM)* |
|---|---|---|
| 101,230 | 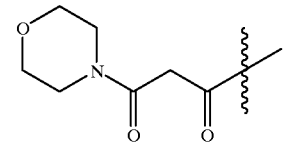 | 70 |
| — | 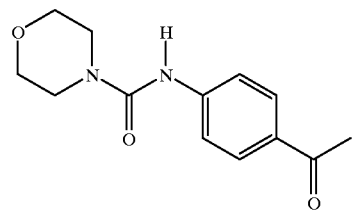 | 28 |
| 100,867 | 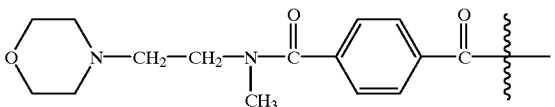 | 43 |
| — | 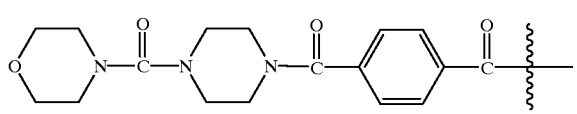 | 19 |
| — | | 24 |
*for human neutrophil elastase, using N-MeOSucAlaAlaProVal-pNA as substrate
TABLE 2A
| MDL # | $P_2$ | $K_i$(nM)* |
|---|---|---|
| 104,339 | (D,L)Tic | 100 |
| 103,773 | (L)Tic | 120 |
| 103,600 | (L)Tca | 70 |
*for human neutrophil elastase, using N-MeOSucAlaAlaProVal-pNA as substrate TABLE 3
SUMMARY OF ORALLY ACTIVE ELASTASE INHIBITORS
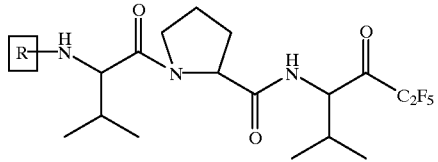
| MDL Number | R | $K_i$ (nM) | Dose (mg/kg) | % Inhibition | animal |
|---|---|---|---|---|---|
| 102,111 | 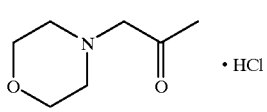 | 170 | 100<br>50<br>25<br>10 | 79*<br>70*<br>61*<br>30 | rat |
| 100,948A | 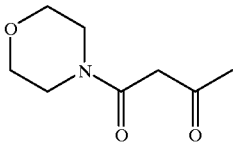 · HCl | 60 | 50<br>10 | 77*<br>39 | rat |
| 101,230 | 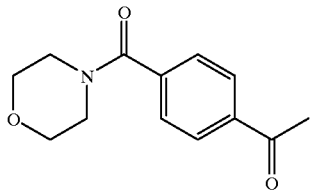 | 70 | 25<br>10 | 41<br>0 | rat |
| 101,146 | 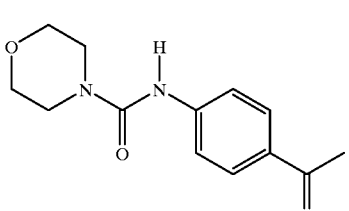 | 20 | 50<br>25<br>10 | 74*<br>56*<br>25 | hamster |
| 100,867 |  | 43 | 50<br>10 | 26<br>0 | rat |

TABLE 3-continued

SUMMARY OF ORALLY ACTIVE ELASTASE INHIBITORS

| MDL Number | R | $K_i$ (nM) | Dose (mg/kg) | % Inhibition | animal |
|---|---|---|---|---|---|
| 101,773 | (CH₃)₂N-C(O)- group | 261 | 50 | 70* | rat |
| 102,823 | tetrahydropyran-4-yl-C(O)- group | 59 | 50 | 71* | rat |
| — | 2-furoyl-C(CH₃)₂- group | 190 | 50 | 44 | rat |
| — | morpholino-C(O)-pyridin-2,5-diyl-C(O)- group | 28 | 25 | 61* | hamster |
| — | morpholino-(CH₂)₂-N(CH₃)-C(O)-phenyl-C(O)- group | 19 | 25 | 17 | hamster |
| — | morpholino-C(O)-piperazinyl-C(O)-phenyl-C(O)- group | 24 | 25 | 31 | hamster |

*means significant at P < .05

In general, the compounds of formula I may be prepared using standard chemical reactions analogously known in the art. The procedure for preparing the formula I compounds wherein B is —CO— is outlined in Scheme A wherein $P_1$, $P_2$, $P_3$, and $P_4$ are as previously defined or are functional equivalents of these groups and Pg is an amino protecting group such as a carbamate, preferably a t-butyloxycarbonyl (Boc) group. The compounds of Formula I wherein B is other than —CO— can be prepared analogously, merely by substituting the appropriate intermediate, which can be the corresponding acid or sulphonyl chloride or the acid for the compound of formula 6 in Scheme A.

SCHEME A

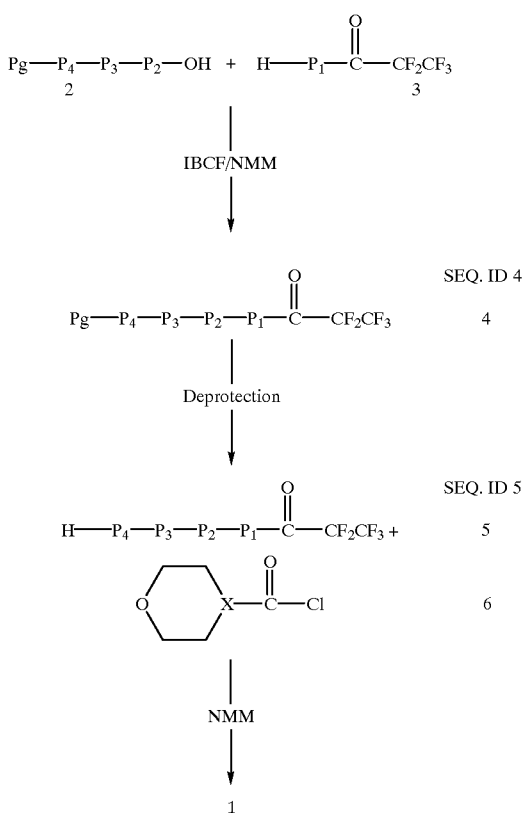

Specifically the compounds of this invention are prepared by coupling of the amino terminal amino unprotected pentafluoroethyl compounds of formula 5 with acid chloride, 6, in the presence of from one to four molar equivalents of a suitable amine which can act as a hydrogen halide acceptor. Suitable amines for use as hydrogen halide acceptors are tertiary organic amines such as tri-(lower alkyl)amines, for example, triethylamine, or aromatic amines such as picolines, collidines, and pyridine. When pyridines, picolines, or collidines are employed, they can be used in high excess and act therefore also as the reaction solvent. Particularly suitable for the reaction is N-methylmorpholine ("NMM"). The coupling reaction can be performed by adding an excess, such as from 1–5, preferably about a 4-fold molar excess of the amine and then the acid chloride, to a solution of the formula 5 pentafluoroethyl ketone. The solvent can be any suitable solvent, for example, petroleum ethers, a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethylether, tetrahydrofuran, or 1,4-dioxane, or an aromatic solvent such as benzene, toluene, or xylene. Methylene chloride is the preferred solvent for this coupling reaction. The reaction is allowed to proceed for from about 15 minutes to about 6 hours, depending on the reactants, the solvent, the concentrations, and other factors, such as the temperature which can be from about 0° C. to about 60° C., conveniently at about room temperature, i.e. 25° C. The formula 1 product can be isolated from the reaction mixture by any appropriate techniques such as by chromatography on silica gel eluting with, for example, a mixture of acetone and ethyl acetate.

The formula 5 pentafluoroethyl peptide can be prepared by, for example, protecting group removal from the corresponding formula 4 pentafluoroethyl peptide which is in turn prepared by the reaction of the formula 2 di- or tri-peptide and the pentafluoroethyl derivative of the $P_1$ amino acid, 3. The reaction of the formula 2 di- or tri-peptide with the formula 3 compound can be promoted by procedures known to promote peptide amide bond formation, such as by reacting the formula 2 di- or tri-peptide with isobutyl chloroformate ("IBCF") preferably in the presence of a HCl acceptor such as mentioned above, preferably NMM, and then adding the formula 3 compound. The reaction of the formula 2 peptide with IBCF is performed by, for example, adding about an equimolar amount of IBCF to a cooled (−10 to −20° C.) solution of the formula 2 peptide and up to about 5 molar equivalents of NMM. After a short time (15 minutes to several hours), the formula 3 peptide is added and the reaction is allowed to proceed for from about 30 minutes to about 10 hours depending on the reactants, the solvent and concentration of reactants. After this initial reaction period the reaction is allowed to warm to room temperature. The product is isolated in any convenient manner such as by washing the reaction mixture with acid, mild base solution such as dilute sodium bicarbonate solution, and brine, and subsequently drying the organic phase and subsequently by evaporation of any solvent. Solvents for this reaction can be any convenient and appropriate solvent such as those mentioned above and preferably will be methylene chloride or a methylene chloride/acetonitrile mixture.

The protecting group is removed from the formula 4 compound in any appropriate manner and the procedure will, of course, depend on the nature of the protecting group and the nature of any other reactive groups on the compound. For example, when the protecting group is a t-butyloxycarbonyl (Boc) group, the formula 4 compound can be converted to the formula 5 compound salt by treatment with gaseous hydrogen chloride in ethyl actate. When the protecting group is a carbobenzyloxy (Cbz) group, the formula 4 compound can be converted to the formula 5 compound by catalytic hydrogenation.

The formula 2 peptide is prepared by sequentially coupling the requisite amino acids using conventional techniques. In some instances the required di- and tri-peptides are commercially available.

In coupling individual amino acids or peptides, appropriate side chain protecting groups are employed. The selection and use of an appropriate protecting group for these side chain functionalities is within the ability of those skilled in the art and will depend upon the amino acid to be protected and the presence of other protected amino acid residues in the peptide. The selection of such a side chain protecting group is critical in that it must not be removed during the deprotection and coupling steps of the synthesis. For example, when Boc is used as the α-amino protecting group, the following side chain protecting groups are suitable: p-toluenesulfonyl (tosyl) moieties can be used to protect the amino side chains of amino acids such as Lys; and a 2-bromocarbobenzoxy (2Br—Z) moiety can be used to protect the hydroxy containing side chains of amino acids such as Tyr. These side chain protecting groups are added and removed according to standard practices and procedures well known in the art. It is preferred to deprotect these side chain protecting groups with a solution of anisole in anhydrous hydrogen fluoride (1:10). Typically, deprotection of side chain protecting groups is performed after the peptide chain synthesis is complete but these groups can alternatively be removed at any other appropriate time. It is preferred to deprotect these side chains at the same time as the peptide is cleaved from the resin when solid phase synthetic methods are employed.

The formula 3 pentafluoroethyl derivative of the $P_1$ amino acid can be prepared as described in European Patent Application Serial Number 90114250, published Jan. 30, 1991.

The compounds are then isolated and purified by standard techniques. The desired amino acids, derivatives and isomers thereof can be obtained commercially or can be synthesized according to standard practices and procedures well known in the art.

The following specific examples are given to illustrate the preparation of various compounds of this invention although the scope of the invention is not meant to be limited to the scompounds exemplified below. Procedures for making the following compounds are also disclosed in M. Angelastro et al., *J. Med. Chem.* 37, 4538–4553 (1994), said reference being incorporated by reference as if fully set forth.

EXAMPLE 1

Preparation of MC-Val-Pro-Val-$CF_2CF_3$

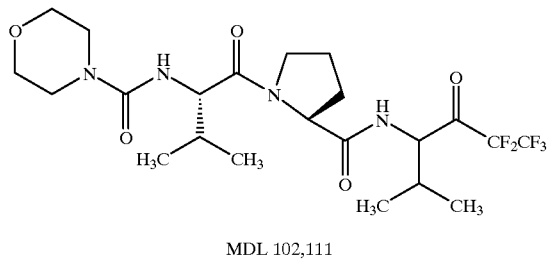

MDL 102,111 a) Preparation of Boc-Val-Pro-Val-$CF_2CF_3$

To a stirred solution of Boc—Val—Pro—OH (1.10 g, 3.5 mmole) in $CH_2Cl_2$ (20 ml) under argon, cooled to −17° C., was added NMM (0.40 ml, 3.68 mmole). After 5 minutes, 1 equivalent (0.45 ml, 3.5 mmole) of IBCF was added and a light suspension formed several minutes later. After 20 minutes NMM (0.4 ml, 3.68 mmol) was added followed by a suspension of H-Val-$CF_2CF_3$.HCl (0.88 g, 3.50 mol) in $CH_2Cl_2$ (10 ml) plus $CH_3CN$ (10 ml) dropwise (from an addition funnel) over ca. 15 minutes. The reaction was stirred at −14 to −18° C. for 1 hour and then the cooling bath was removed. The reaction was allowed to warm to room temperature (ca. 40 min.) and diluted with $CH_2Cl_2$ (100 ml). The organic phase was washed with 1 N HCl (3×75 ml), satd. $NaHCO_3$ (2×75 ml), and brine (50 ml). Drying ($Na_2SO_4$) and concentration gave a colorless oil which was placed under high vacuum to give the desired product as a white foam (1.59 g, 88%). Elemental analysis; calculated for $C_{22}H_{34}F_5N_3O_5$: %C=51.26; %H=6.65; %N=8.15. Found: %C=50.80; %H=6.57; %N=7.85.

b) Preparation of H-Val-Pro-Val-$CF_2CF_3$.HCl

Into a stirred solution of the product of part (a) (1.52 g, 2.95 mmole) in ethyl acetate (75 ml) cooled in an ice-water bath was bubbled HCl gas for 10 minutes, after which the reaction flask was capped with a septum. TLC after 1 hour indicated the absence of starting material. The reaction mixture was concentrated, the residue dissolved in ethyl acetate and concentrated (2×) to give a white solid which was dried under high vacuum over KOH pellets. Dried weight was 1.35 g.

Elemental Analysis; Calcd for $C_{17}H_{26}F_5N_3O_3$.HCl: %C=45.19; %H=6.02; %N=9.30. Found: %C=44.84; %H=6.22; %N=8.88. High resolution mass spectrum calcd for $C_{17}H_{27}F_5N_3O_3$ (MH$^+$)=416.1973; found MH$^+$= 416.1972; error=−0.2 ppm.

c) Preparation of MC-Val-Pro-Val-$CF_2CF_3$

To a stirred solution of the product of part (b) (1.06 g, 2.35 mmole) in $CH_2Cl_2$ (100 ml) under argon was added 4-morpholinecarbonyl chloride (1.09 ml, 9.38 mmole) followed by NMM (0.52 ml, 4.69 mmole). After 105 minutes, the reaction mixture was concentrated to ca. 5 ml and loaded onto a column for chromatography. Flash chromatography (6.5×12 cm silica gel column), eluting with acetone/EtOAc (30:70), gave an oil. A mixture of ethyl ether and hexane was added and concentrated to give a white solid (0.78 g). TLC: $R_f$ 0.33 (35:65 acetone:EtOAc). $^1$H NMR: δ 7.90 (br d, J=7.7 Hz, 1/8H, NH), 7.53 (br d, J=7.7 Hz, 7/8H, NH), 5.10 (br d, J=8.7 Hz, 1H, NH), 4.99–4.92 (m, 1H, α-CH of Val), 4.71 (dd, J=7.9, 1.9 Hz, 1/8H, NH of Pro), 4.61 (dd, J=8.0, 2.7 Hz, 7/8H, NH of Pro), 4.49 (dd, J=8.7, 7.0 Hz, 1H, α-CH of Val), 4.95–4.76 and 3.68–3.57 (pr m, 2H, $CH_2N$), 3.69 (t, J=5.1 Hz, 4H, $CH_2OCH_2$), 3.47–3.24 (m, 4H, $CH_2NCH_2$), 2.53–2.25 and 2.19–1.81 (pr m, 6H, 2×β-CH and $CH_2CH_2$), 1.12–0.83 (m, 12H, 4×$CH_3$). $^{19}$F NMR: δ −82.25 (s, $CF_3$, major isomer), −82.30 (s, $CF_3$, minor isomer), −121.70 and −122.72 (AB quartet, J=296 Hz, $CF_2$, major isomer), −121.64 and −122.82 (AB quartet, J=296 Hz, $CF_2$, minor isomer). MS (DCI/$CH_4$): m/z (rel intensity) 529 (MH$^+$, 57), 345 (18), 317 (60), 214 (18), 213 (100), 185 (32). Elemental Analysis; calcd for $C_{22}H_{33}F_5N_4O_5$: %C=50.00; %H=6.29; %N=10.60. Found: %C=49.88; %H=6.59; %N=10.62.

EXAMPLE 2

Preparation of N-[4-(4-Morpholinylsulfonyl) benzoyl]-L-valyl-N-[3,3,4,4,4-pentafluoro-1-(1-methylethyl)-2-oxobutyl]-L-prolinamide

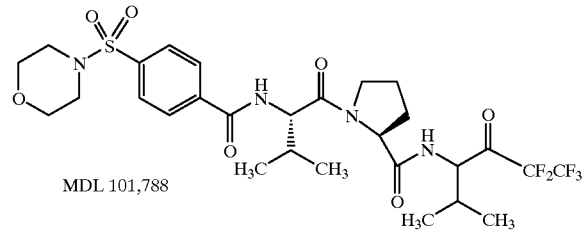

MDL 101,788

To a solution of diisopropylethylamine (1.76 g, 13.6 mmol, 2.37 ml) and morpholine (1.98 g, 22.7 mmol, 1.98 ml) in THF (40 ml) was added, dropwise over 0.5 h, a solution of 4-(chlorosulfonyl)benzoic acid (2.50 g, 11.3 mmol) in THF (17 ml). After stirring at room temperature for 18 h the reaction was poured into $H_2O$ (150 ml) and washed with EtOAc. The aqueous layer was acidified (pH 1) with concentrated HCl, and the precipitate collected, washed with cold $H_2O$, and dried under vacuum over $P_2O_5$ to give 2.68 g (87%) of 4-(4-morpholinylsulfonyl)-benzoic acid as an off-white solid.

To a solution of the benzoic acid derivative prepared above (0.240 g, 0.885 mmol) and NMM (0.446 g, 4.43 mmol, 0.489 ml) in CH$_2$Cl$_2$ (8.9 ml) at -22° C. under N$_2$ was added IBCF (0.121 g, 0.885 mmol, 0.115 ml), and the reaction stirred at -22° C. for 20 min. The HCL.Val-Pro-Val-C$_2$F$_5$ (0.400 g, 0.885 mmol) was added in several portions, and the reaction was stirred at -22° C. for 0.5 h, followed by 4 h at room temperature. The reaction was diluted with CH$_2$Cl$_2$ (30 ml) and then washed successively with 10% HCl (2×15 ml), sat. NaHCO$_3$ (2×15 ml), brine (1×15 ml), and dried over MgSO$_4$. Solvent removal under vacuum gave an off-white foam which was purified by flash chromatography (silica gel; 25/75, hexane/EtOAc) to give 0.295 g (50%) of the title compound as a white solid. TLC: R$_f$ 0.49 (EtOAc). $^1$H NMR: δ8.02–7.93 (m, 2H, aryl), 7.85–7.77 (m, 2.25H, aryl and NH), 7.70 (d, J=7.3 Hz, 0.75H, NH), 6.93 (d, J=9.0 Hz, 1H, NH), 5.04–4.96 (m, 1H, α-CH of Val), 4.86 (dd, J=8.7, 6.7 Hz, 1H, α-CH of Val), 4.71 (dd, J=8.1, 2.0 Hz, 0.25H, α-CH of Pro), 4.61 (dd, J=8.1, 3.0 Hz, 0.75H, α-CH of Pro), 3.92–3.64 (m, 6H, CH$_2$OCH$_2$ and CH$_2$N of Pro), 3.07–2.96 (m, 4H, CH$_2$NCH$_2$), 2.55–1.82 (series of m, 6H, 2×β-CH of Val, CH$_2$CH$_2$ of Pro), 1.12–0.85 (m, 12H, 4×CH$_3$). $^{19}$F NMR: δ–82.12 (s, CF$_3$, major), -82.16 (s, CF$_3$, minor), -121.50 and -122.74 (AB quartet, J=296 Hz, CF$_2$, minor), -121.56 and -122.60 (AB quartet, J=299 Hz, CF$_2$, major). MS (DCI/CH$_4$): m/z (rel intensity) 669 (MH$^+$, 55), 317 (100). Anal. (C$_{28}$H$_{37}$F$_5$N$_4$O$_7$S.0.33H$_2$O): C, H, N: calcd, 8.30; found, 7.82.

EXAMPLE 3

Preparation of N-[3-Methyl-2-(4-morpholinocarbonyl)-1-oxobutyl]-Val-Pro-Val-CF$_2$CF$_3$

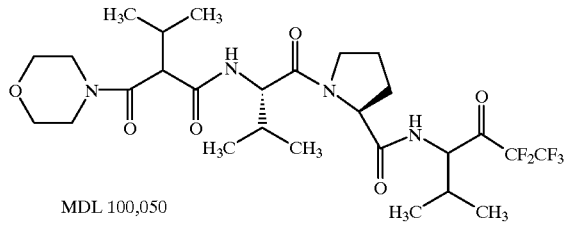

MDL 100,050 a) Preparation of methyl 2-(4-morpholinocarbonyl) acetate

To a solution of methylmalonylchloride (10.0 g, 73.2 mmol) in CH$_2$Cl$_2$ (200 ml) at 0° C. under N$_2$ was added rapidly dropwise a solution of morpholine (16.0 g, 0.183 mmol, 16.0 ml) in CH$_2$Cl$_2$ (50 ml), and the reaction stirred at room temperature for 4 h. The reaction was filtered, the filtrate diluted with additional CH$_2$Cl$_2$ (200 ml), and then washed successively with 10% HCl, sat. NaHCO$_3$, brine, and dried over MgSO$_4$. Solvent removal in vacuo gave a yellow oil which was purified by flash chromatography (silica gel, EtOAc) to give 9.70 g (71%) of the title compound, 1, as a pale yellow oil.

b) Preparation of methyl 3-methyl-2-(4-morpholinocarbonyl)butanoate

To a solution of the compound prepared in Example 3a (9.70 g, 51.8 mmol) in THF at 0° C. under N$_2$ was added NaH (1.71 g, 07.0 mmol, 80% dispersion in mineral oil) in three portions. After the initial reaction subsided the reaction was allowed to warm to room temperature, the isopropyl iodide (13.2 g, 77.7 mmol, 7.77 ml) added, and the reaction heated at 60° C. for 8 h followed by 64 h at room temperature. The reaction was diluted with CH$_2$Cl$_2$ (30 ml) and then washed with H$_2$O, brine, and dried over MgSO$_4$. Solvent removal in vacuo gave a brown oil which was purified by flash chromatography to yield 7.70 g (65%) of the title compound as an orange oil.

c) Preparation of 3-Methyl-2-(4-morpholinocarbonyl)-butanoic acid

To a solution of the compound prepared in Example 3b (7.70 g, 33.6 mmol) in MeOH (150 ml) was added LiOH (37 ml), 1 M in H$_2$O ) and the reaction stirred at room temperature for 24 h. The reaction was acidified with conc. HCl and the solvent removed in vacuo. The residue was triturated with hexane, collected on a fritted funnel, washed with several portions of hexane, and dried in vacuo over P$_2$O$_5$ to give 5.82 g (81%) of the title compound as a white solid.

d) Preparation of N-[3-Methyl-2-(4-morpholinocarbonyl-1-oxobutyl]-Val-Pro-Val-CF$_2$CF$_3$ To a suspension of the compound prepared in Example 3c (0.304 g, 1.33 mmol) in CH$_2$Cl$_2$ (8.9 ml) under N$_2$ was added N-methylmoprpholine (0.446 g, 4.43 mmol, 0.489 ml), and the resulting clear, colorless solution cooled to -22° C. The IBCF (0.182 g, 1.33 mmol, 0.173 ml) was added and the reaction stirred for 20 min, followed by addition of the HCl. Val-Pro-Val-C$_2$F$_5$ in one portion. After stirring at -22° C. for 4 h the reaction was diluted with additional CH$_2$Cl$_2$ (35 ml) and washed successively with 10% HCl (3×20 ml), sat. NaHCO$_3$ (2×20 ml), brine (1×20 ml), and dried over MgSO$_4$. Solvent removal in vacuo followed by purification by flash chromatography (silica gel; 20/80, acetone/EtOAc) gave 0.343 g (63%) of the title compound as a white foam.R$_f$ 0.49 (3:7 acetone:EtOAc). $^1$H NMR: δ7.95 (br d, J=7.5 Hz, 0.2H, P$_1$—NH), 7.65 (br d, J=8.5 Hz, 0.5H, P$_4$—NH), 7.59 (br d, 7.5 Hz, 0.8H, P$_1$-NH), 7.17 (br d, J=8.5 Hz, 0.5H, P$_4$—NH), 4.95–4.87 (m, 1H, α-CH of Val), 4.71 (dm, J=8.0 Hz, 0.2H, α-CH of Pro), 4.53–4.42 (m, 1H, α-CH of Val), 3.91–3.47 (m, 10H, NCH$_2$ of Pro and 2×OCH$_2$CH$_2$N), 3.17 (d, J=9.7 Hz, 0.5H, α-CH of P$_4$), 3.15 (d, J=10.3 Hz, 0.5H, α-CH of P$_4$), 2.54–1.69 (m, 7H, β-CH of P$_4$, 2×β-CH of Val and CH$_2$CH$_2$ of Pro), 1.11–0.84 (m, 18H, 6×CH$_3$). $^{19}$F NMR: δ–82.13 (s, CF$_3$, major), -82.18 (s, CF$_3$, minor), -121.56 and -122.52 (AB quartet, J=293 Hz, CF$_2$, major), -121.56 and -122.62 (AB quartet, J=293 Hz, CF$_2$, minor). IR (film): 3304, 2968, 2936, 1753, 1641, 1528, 1439 cm$^{-1}$. MS (DCI/CH$_4$): m/z (rel intensity) 613 (MH$^+$, 53), 317 (89), 297 (100), 269 (31). Anal. (C$_{27}$H$_{41}$F$_5$O$_6$.0.25H$_2$O): C, H, N.

EXAMPLE 4

Alternative Preparation of Boc-Val-CF$_2$CF$_3$

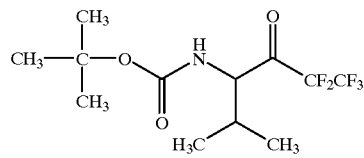

MDL 101,286

A mixture of 288.0 g (1.11 mol) of Boc-Val N-methyl-O-methyl hydroxamic acid and 4.7 L of anhydrous Et$_2$O was charged to a 12-L 3-necked flask fitted with a stirrer, thermometer, dry ice condenser, gas dispersion tube and continuous $N_2$ purge. The resulting solution was cooled to −60° C. to −65° C. A total of 885.2 g (3.60 mol) of $C_2F_5I$ was added via a gas dispersion tube over about 30 min to the solution of Boc-Val N-methyl-O-methyl hydroxamic acid while maintaining a temperature of about −65° C. Immediately upon completing the gas addition, a total of 2.39 L of 1.5M $CH_3Li.LiBr$ in $Et_2O$ (3.59 mol) was added over 1 h maintaining a reaction temperature of −52° C. to −58° C. A precipitate formed after about ⅓ of the $CH_3Li.LiBr$ had been added but a complete solution was present at the end of the addition. The resulting solution was stirred at −52° C. to −58° C. for 1 h. The reaction was monitored by GC ($R_t$ of MDL 101,286=1.3 min, $R_t$ of Boc-Val N-methyl-O-methyl hydroxamic acid=5.1 min) and found to contain 7.2% of Boc-Val N-methyl-O-methyl hydroxamic acid. A total of 255 mL (3.47 mol) of acetone was added over about 15 min maintaining a reaction temperature of −52° C. to −58° C. and the resulting mixture was stirred for 10 min. The mixture was quenched into a 22 L flask containing 4.7 L of 0.75M $KHSO_4$ which had been cooled to about 0° C. The organic layer was separated and washed with 3 L of $H_2O$. The organic layer was dried using 500 g of $MgSO_4$ and filtered to remove the drying agent. The filtrate was concentrated at 40° C./100 torr to a semi-solid weighing 409 g. The crude material was dissolved in 1.2 L of hexane at 45° C. and cooled slowly over about 30 min to −25° C. to −30° C. The solid which crystallized was filtered off and washed with 250 mL of hexane at −30° C. The MDL 101,286 obtained was vacuum dried (25° C./100 torr) to give 176.7 g. The filtrate was concentrated at 35° C./100 torr to a residue weighing 153.5 g. The material was put on a Kugelrohr distillation apparatus and a forerun was collected up to 40° C./0.6 torr. The receiver was changed and a total of 100.5 g of crude MDL 101,286 was collected at 40° C.–60° C./0.6 torr. The crude product was dissolved in 500 mL of hexane at about 50° C. The resulting solution was cooled to −30° C. The solid which crystallized was filtered off and washed with 100 mL of cold (−30° C.) hexane. The product was vacuum dried at 25° C./100 torr to give another 68.0 g of MDL 101,286 for a total yield of 244.7 g (70% yield) which was 99.9% pure by GC.

Anal. Calcd. for $C_{12}H_{18}F_5NO_3$ (319.28): C, 45.14, H, 5.68, N, 4.39; Found: C, 45.30; 45.49; H, 5.50, 5.58; N, 4.26, 4.35.

EXAMPLE 5

Preparation of N-[(Tetrahydro-2H-pyran-4-yl) carbonyl]-L-valyl-N-[3,3,4,4,4-pentafluoro-1-methylethyl)-2-oxobutyl]-L-prolinamide

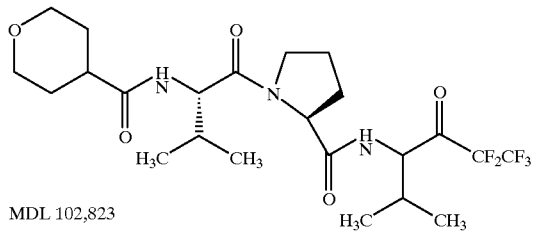

MDL 102,823 a) Preparation of (S)-[1-[(Methoxymethylamino) carbonyl]-2-methylpropyl]carbamic Acid, 1,1-Dimethyl Ester To a solution of N-(tert-butoxycarbonyl)-L-valine (11.3 g, 52.2 mmol) in $CH_2Cl_2$ (200 mL) was added DMAP (6.37 g, 52,2 mmol), N,O-NMM (5.27 g, 52,2 mmol, 5.73 mL), and EDCI (10.0 g, 52.2 mmol), and the solution was stirred at room temperature for 20 h. The solution was washed with 10% HCl (4×150 mL), saturated $NaHCO_3$ (3×150 mL), and brine (1×150 mL), and the solvent was removed in vacuo to give 12.6 g (93%) of the title compound as a clear, colorless oil.

b) Preparation of (S)-[3,3,4,4,4-Pentafluoro-1-(1-methylethyl)-2-oxobutyl]-carbamic Acid, 1,1-Dimethyl Ester To a −78° C. solution of the compound of example 5 (a) (10.0 g, 38.4 mmol) in $Et_2O$ (1 L) was added condensed pentafluoroethyl iodide (28.98 g, 118.29 mmol). To the mixture was added methyllithium-lithium bromide complex (78 mL, 117.0 mmol) at a rate which maintained an internal reaction temperature below −65° C. The reaction mixture was stirred at −65° C. to −78° C. for 1.5 h, the cold bath removed, and stirring continued for 15 min during which time the internal temperature rose to −40° C. The mixture was poured into $H_2O$ (1 L), and the aqueous phase was acidified with potassium hydrogen sulfate. The aqueous phase was extracted with additional $Et_2O$ (500 mL), and the combined organic extracts were washed with saturated $NaHCO_3$ and dried over $Na_2SO_4$. The solvent was removed in vacuo, and the crude product was loaded onto silica gel (225 g) and eluted with hexane/EtOAc (25:1) to give the title compound (10.4 g, 85%) as a white solid. $^1H$ NMR: δ4.98 (br d, 1H, NH), 4.80 (dd, 1H, CH), 2.29 (m, 1H, β-CH), 1.44 (s, 9H, t-Bu), 1.07 (d, J=6.6 Hz, 3H, $CH_3$), 0.85 (d, =6.6 Hz, 3H, $CH_3$). $^{13}C$ NMR: δ194.89 (t, J=27.1 Hz), 177.65, 117.84 (qt, J=288.6, 34.1 Hz), 107.05 (tq, J=269.5, 38.1 Hz), 80.59, 60.60, 28.97, 27.85, 19.57, 15.90. $^{19}F$ NMR: δ−82.3 (s, $CF_3$), −121.7 and −123.0 (AB quartet, J=296 Hz, $CF_2$), HRMS ($C_{12}H_{19}F_5NO_3$) (MH$^+$): calcd, 320.1285; obsd, 320.1310.

c) Preparation of (S)-4-Amino-1,1,1,2,2-pentafluoro-5-methyl-3-hexanone, Hydrochloride Salt Into a stirred solution of the compound of example 5 (b) (14.2 g, 44.4 mmol) in EtOAc (300 mL) cooled in an ice-water bath was bubbled HCl gas for 7 min. Bubbling was ceased, and the reaction mixture was capped with a drying tube. After 1 h, the solution was allowed to warm to room temperature. The solution was concentrated, 300 mL of $Et_2O$/hexane (1:1) was added to the gelatinous residue, and the mixture was concentrated to give an off-white solid. The solid was triturated with $Et_2O$ (300 mL), crushed, and filtered to give the title compound (10.7 g, 96%) as a white solid. $^1H$ NMR: δ9.07 (br s, 3H, $NH_3$), 4.73 (d, 1H, CH), 2.70–2.53 (m, 1H, CH), 1.35 (d, 3H, $CH_3$), 1.07 (D, 3H, $CH_3$). $^{19}F$ NMR: δ−82.16 (S, $CF_3$), −120.59 AND −122.69 (AB quartet, J=300 Hz, $CF_2$). MS (DCI/$CH_4$): m/z (rel intensity) 439 (dimer MH$^+$, 22), 220 (MH$^+$, 100), 200 (23), 178 (50), 72 (33). HRMS ($C_7H_{11}F_5NO$) (MH$^+$): calcd, 220.0761; obsd, 220.0759.

d) Preparation of N-[(1,1-Dimethylethoxy) carbonyl]-L-valyl-N-[3,3,4,4,4-pentafluoro-1-(1-methylethyl)-2-oxobutyl]-L-prolinamide To a solution of N-(tert-butoxycarbonyl)-L-valyl-L-proline (6.15 g, 19.6 mmol) and NMM (1.98 g, 19.6 mmol, 2.15 mL) in $CH_2Cl_2$ (300 mL) at −20° C. was added IBCF (2.67 g, 19.6 mmol, 2.54 mL) at an internal temperature of −18° C. After stirring for 20 min, an additional equivalent of NMM (1.98 g, 19.6 mmol, 2.15 mL) was added followed by the addition of the compound of example 5 (c) (5.00 g, 19.6 mmol) in several portions at an internal temperature of −17° C. Stirring was continued at −20° C. for 1 h. Cooling was discontinued, and upon reaching room temperature, the solution was diluted with $CH_2Cl_2$ (250 mL) and washed with 1 N HCl (4×200 mL), saturated $NaHCO_3$ (2×200 mL), and brine (1×200 mL). Solvent removal in vacuo gave 8.89 g of an off-white foam. Flash chromatography (10×25 cm silica gel column eluting with a gradient of 25–50% EtOAc in hexane) gave 8.05 g (80%; 97:3 L-L-L:L-L-D by $^1H$ NMR) of the title compound as a white solid foam. TLC: $R_f$ 0.56 (1:1 hexane:EtOAc). $^1H$ NMR: δ7.57 (br d, J=7.6 Hz, 1H, NH), 5.22 (br d, J=9.3 Hz, 1H, NH), 4.94 (dd, J=7.6, 4.4 Hz, 1H, CH of Val), 4.63 (dd, J=8.1, 2.8 Hz, 1H, CH of Pro), 4.28 (dd, J=9.3, 6.5 Hz, 1H, CH of Val), 3.81–3.69 and 3.64–3.54 (pr m, 2H, $CH_2N$), 2.44–1.81 (series of m, 6H, 2×β-CH of Val, $CH_2CH_2$), 1.44 (s, 9H, t-Bu), 1.02 (d, J=6.8 Hz, 3H, $CH_3$), 0.98 (d, J=6.8 Hz, 3H, $CH_3$), 0.95 (d, J=6.8 Hz, 3H, $CH_3$), 0.88 (d, J=6.8 Hz, 3H, $CH_3$). $^{19}F$ NMR: δ−82.15 (s, $CF_3$), −121.70 and −122.70 (AB quartet, J=296 Hz, $CF_2$). MS ($DCI/CH_4$): m/z (rel intensity) 556 ($M+C_3H_5^+$, 5), 544 ($M+C_2H_5^+$, 19), 516 ($MH^+$, 52), 496 (4), 460 ($MH-C_4H_8^+$, 100), 440 (11), 416 (26), 396 (6). Anal. ($C_{22}H_{34}F_5N_3O_5$): C, H, N.

e) Preparation of N-L-Valyl-N-[3,3,4,4,4-pentafluoro-1-(methylethyl)-2-oxobutyl]-L-prolinamide, Hydrochloride Salt Into a stirred solution of the product of example 5 (d) (7.88 g, 15.3 mmol) in EtOAc (250 mL) cooled in an ice-water bath was bubbled HCl gas for 9 min. The bubbling was ceased, and the reaction mixture was capped with a drying tube. After 1 h, the reaction mixture was allowed to warm to room temperature and concentrated. EtOAc (100 mL) and hexane (100 mL) were added to the residue, and the mixture was concentrated again. The residue was dissolved in the minimum amount of hot EtOAc (ca. 15 mL) and added slowly to rapidly stirred hexane (750 mL). Filtration and drying under vacuum over KOH pellets gave the title compound (6.32 g, 91%; greater than 97% L-L-L by $^{19}F$ NMR) as a white solid. $^1H$ NMR δ8.48–8.13 (m, 3H, $NH_3$), 7.75 (br d, 1H, NH), 4.95 (dd, 1H, CH), 4.83–4.70 (m, 1H, CH), 4.07–3.92 (m, 1H, CH), 3.92–3.78 and 3.64–3.51 (pr m, 2H, $CH_2N$), 2.43–1.96 (m, 6H, 2×CH and $CH_2CH_2$), 1.12 (overlapping pr d, 6H, 2×$CH_3$), 1.02 (d, 3H, $CH_3$), 0.92 (d, 3H, $CH_3$). $^1F$ NMR: δ−82.31 (s, $CF_3$), −122.44 (s, $CF_2$). MS ($DCI/CH_4$): m/z (rel intensity) 416 ($MH^+$, 100), 396 (10), 317 (22), 197 (8), 169 (8), 72 (10). Anal. ($C_{17}H_{26}F_5N_3O_3 \cdot HCl \cdot 0.75H_2O$): C, H, N.

f) Preparation of Tetrahydro-4-(methoxymethylene)-2H-pyran

To a stirred suspension of (methoxymethyl)triphenylphosphonium chloride (24.82 g, 72.41 mmol) in THF (250 mL) cooled in an ice-water bath was added n-BuLi (24.76 mL or 2.42 M solution in hexane, 59.93 mmol). The reaction mixture was allowed to warm to room temperature for 1 h and then recooled in an ice-water bath and a solution of tetrahydro-4H-pyran-4-one (5.00 g, 49.94 mmol) in THF (10 mL) added. After 20 min the reaction mixture was concentrated to an oily reside, the residue was triturated with $Et_2O$ (150 mL), and the supernatant was decanted. This process was repeated (6×75 mL), and the combined supernatants were concentrated to give crude title compound (7.3 g) as an orange oil. Flash chromatography (10×18 cm) eluting with a gradient (5–10%) of EtOAc/hexane gave the title compound (2.25 g, 35%) as a volatile, colorless oil. TLC: $R_f$ 0.13 (5:95 EtOAc:hexane). $^1H$ NMR: δ5.85 (s, 1H, vinyl), 3.69–3.61 (m, 4H, $CH_2OCH_2$), 3.56 (s, 3H, $OCH_3$), 2.32 and 2.06 (pr t, 4H, 2×$CH_2$).

g) Preparation of Tetrahydro-2H-pyran-4-carboxylic Acid

To a stirred solution of the product of example 5 (f) (2.24 g, 17.48 mmol) in acetone (35 mL) was added 1.0 N HCl (1 mL). After 3 h, TLC indicated that the product of example 5 (f) had been consumed and a new, lower $R_f$ material (presumably aldehyde) had been formed. The solution was diluted with additional acetone (65 mL) and treated with Jones reagent until a brown color persisted in the supernatant. The reaction mixture was concentrated to ca. 4 L and flash chromatographed (6×16 cm column) eluting with a gradient (75–100%) of EtOAc/hexane to give the title compound (1.11 g, 49%) as a white solid. Mp: 86–88° C. (lit.[48] mp 87° C.). $^1H$ NMR: δ10.84 (br s, 1H, $CO_2H$), 3.99 (dt, J=11.6, 3.6 Hz, 2H 1/2$CH_2OCH_2$), 3.46 (ddd, J=13.7, 10.6, 3.0 Hz, 2H, 1/2$CH_2OCH_2$), 2.59 (tt, J=10.5, 4.5 Hz, 1H, CH), 1.98–1.74 (m, 4H, 2×$CH_2$). $^{13}C$ NMR: δ180.4, 66.9, 39.8, 28.3. MS ($DCI/CH_4$): m/z (rel intensity) 131 ($MH^+$, 38), 114 (17), 113 (100), 86 (22), 85 (99). Anal. ($C_6H_{10}O_3$): C, H.

h) Preparation of N-[(Tetrahydro-2H-pyran-4-yl)carbonyl]-L-valyl-N-[3,3,4,4,4-pentafluoro-1-methylethyl)-2-oxobutyl]-L-prolinamide To a mixture of the product of example 5 (g) (146 mg, 1.12 mmol) and DMF (0.2 mL) in $CH_2Cl_2$ (10 mL) was added oxalyl chloride (142 mg, 1.12 mmol, 0.1 mL). The mixture was stirred at room temperature for 0.5 h, followed by the addition of NMM (287 mg, 2.84 mmol, 0.32 mL) and the product of example 5 (e) (270 mg, 0.60 mmol). The mixture was stirred for 2.5 h, poured into $H_2O$, and extracted with ethyl acetate. The combined extracts were dried and concentrated, and the residue was purified by recrystallization (hexane/ethyl acetate) to yield 252 mg (79%) of the title compound (L-L-L) as a white solid. $^1H$ NMR; δ7.44 (d, J=7.9 Hz, 1H, NH), 6.18 (d, J=8.7 Hz, 1H, NH), 4.98 (ddd, J=7.9, 4.3, 1.0 Hz, 1H, α-CH of Val), 4.62 (m, 2H, α-CH of Val and α-CH of Pro), 4.02 (m, 2H, $CH_2OCH_2$), 3.80 (m, 1H, $NCH_2$), 3.62 (m, 1H, $NCH_2$), 3.41 (m, 2H, $CH_2OCH_2$), 2.45–1.7 (series of m, 11H, CHCON, 2×β-CH of Val, $CH_2CH_2$, and $CH_2CCH_2$), 1.03 (d, J=6.6 Hz, 3H, $CH_3$), 0.99 (d, J=6.6 Hz, 3H, $CH_3$), 0.94 (d, J=6.6 Hz, 3H, $CH_3$), 0.88 (d, J=6.6 Hz, 3H, $CH_3$). $^1F$ NMR: δ−82.15 (s, $CF_3$), −121.61 and −122.66 (AB quartet, J=296 Hz, $CF_2$). IR (KBR): 3303, 3274, 2871, 1751, 1673, 1657, 1639, 1200 $cm^{-1}$. MS ($DCI/CH_4$): m/z (rel intensity) 528 ($MH^+$, 80), 317 (100). HRMS ($C_{23}H_{34}F_5N_3O_5$) ($M^+$): calcd, 527.2418; obsd, 527.2419.

EXAMPLE 6

Preparation of N-[4-(4-Morpholinylcarbonyl)benzoyl]-L-valyl-N-[3,3,4,4,4-pentafluoro-1-(1-methylethyl)-2-oxobutyl]-L-prolinamide

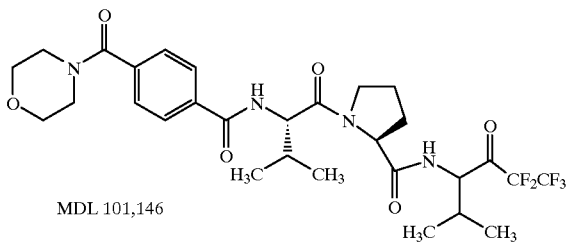

MDL 101,146

To a stirred suspension of 4-(4-morpholinylcarbonyl)-benzoic acid (11.2 g, 47.8 mmol) and benzyltriethylammonium chloride (9 mg, 0.04 mmol; Burdett, K. A., *Synthesis*, 1991, 441–442) in 1,2-dichloroethane (90 mL) was added thionyl chloride (3.49 mL, 47.8 mmol), and the reaction mixture was heated at reflux. After 19 H, the solution was allowed to cool to room temperature and concentrated to give the acid chloride as a light-orange liquid, which was used without further purification. In a separate flask, a stirred solution of the product of example 5 (e) (18.0 g, 39.8 mmol) in $CH_2Cl_2$ (450 mL) was cooled to $-20°$ C. NMM (17.52 mL, 0.16 mmol) was added and immediately followed by the addition of a solution of the acid chloride in $CH_2Cl_2$ (450 mL) was cooled to $-20°$ C. NMM (17.52 mL, 0.16 mmol) was added and immediately followed by the addition of a solution of the acid chloride in $CH_2Cl_2$ (50 mL) at such a rate as to maintain the internal reaction temperature at $-13°$ C. or less. After the addition was complete, the reaction mixture was allowed to warm to room temperature. After an additional 2 h, the reaction mixture was diluted with $CH_2Cl_2$ (500 mL) and washed with 0.5 N HCl (2×500 mL), saturated $NaHCO_3$ (2×500 mL), and brine (250 mL). Drying and concentration gave crude title compound (28.5 g). Recrystallization from EtOAc/hexane followed by flash chromatography (10×20 cm silica gel column) eluting with acetone/EtOAc (1:9) gave the title compound (19.9 g; 88:12 L-L-L:L-L-D by HPLC) as a white solid. Chromatography of the filtrate (6×13 cm silica gel column) eluting with a gradient (0–10%) of acetone/EtOAc gave additional title compound (1.77 g, 86% total; 3:2 L-L-L:L-L-D by HPLC) as a white solid. The 21.7 g of title compound was pooled with other batches and subjected to epimerization.

Epimerization

A solution of the title compound (example 6) (55.7 g, 88.0 mmol) and NMM (8.90 g, 88.0 mmol, 9.68 mL) in $CH_2Cl_2$ (880 mL) was stirred at room temperature for 23 h. The solution was diluted to 1.5 L with additional $CH_2Cl_2$ and washed with 0.5 N HCl (5×400 mL), saturated $NaHCO_3$ (3×400 mL), and brine (400 mL). The organics were concentrated and dried over $P_2O_5$ to give 53.8 g (97%; 49.9:50.1 L-L-L:L-L-D by HPLC) of title compound as a white solid foam. TLC: $R_f$ 0.24 (30:70 acetone: EtOAc). $^1H$ NMR: δ7.92–7.79 and 7.52–7.40 (pr m, 5H, aryl and NH), 6.88 (d, J=9.0 Hz, 1H, NH), 5.02–4.95 (m, 1H, α-CH of Val), 4.71 (dd, J=7.9, 1.9 Hz, 0.5H, CH or Pro), 4.61 (dd, J=7.9, 2.8 Hz, 0.5H, CH or Pro), 3.96–3.27 (m, 10H, 2×$NCH_2Ch_2O$ and $NCH_2$ or Pro), 2.56–1.75 (series of m, 6H, 2×β-CH of Val and $CH_2CH_2$), 1.17–0.82 (m, 12H, 4×$CH_3$). $^{19}F$ NMR: δ−83.12 (s, $CF_3$, isomer I) and −82.17 (s, $CF_3$, isomer II), −121.52 and −122.74 (AB quartet, J =271 Hz, $CF_2$), −121.58 and −122.62 (AB quartet, J=301 Hz, $CF_2$, isomer II). IR (KBr pellet): 3435, 3317, 1630 $cm^{-1}$. MS ($DCI/CH_4$): m/z (rel intensity) 633 ($MH^+$, 13), 317 (100). Anal. ($C_{29}H_{37}F_5N_4O_6$·0.4 $H_2O$): C, H, N.

EXAMPLE 7

Preparation of N-[(Dimethylamino)carbonyl]-L-valyl-N-[3,3,4,4,4-pentafluoro-1-(1-methylethyl)-2-oxobutyl]-L-prolinamide

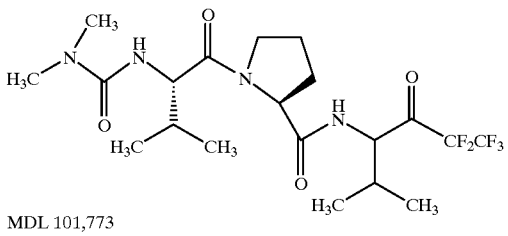

MDL 101,773

To a solution of the compound of example 5 (e) (290 mg, 0.64 mmol) in $CH_2Cl_2$ (20 mL) were added dimethylcarbamyl chloride (274 mg, 2.56 mmol, 0.24 mL) and NMM (130 mg, 1.29 mmol, 0.14 mL). The mixture was stirred for 2.5 h, the solvent concentrated, and the residue purified by flash chromatography (1:3 acetone:EtOAc) to yield 149 mg (48%) of the title compound (3:1 L-L-L:L-L-D) as a white solid.

$^1H$ NMR: δ7.96 (d, J=7.6 Hz, 0.3H, NH), 7.62 (d, J=7.7 Hz, 0.7H, NH), 4.99 (d, J=8.0 Hz, 1H, NH), 4.97–4.90 (m, 1H, α-CH of Val), 4.71 (dd, J=8.0, 2.5 Hz, 0.3H, α-CH of Pro), 4.62 (dd, J=8.0, 2.5 Hz, 0.7H, α-CH of Pro), 4.46 (dd, J=8.7, 7.3 Hz, 1H, α-CH of Val), 3.87 (m, 1H, $NCH_2$), 3.61 (m, 1H, $NCH_2$), 2.94 [s, 6H, $N(CH_3)_2$], 2.50–1.75 (series of m, 6H, 2×β-CH of Val and $CH_2CH_2$), 1.00 (m, 9H, 3×$CH_3$), 0.88 (d, J=6.9 Hz, 2.1H, $CH_3$), 0.89 (d, J=6.9 Hz, 0.9H, $CH_3$). $^{19}F$ NMR: δ−82.16 (s, $CF_3$, major isomer) and −82.21 (s, $CF_3$, minor isomer), −121.61 and −122.61 (AB quartet, J=296 Hz, $CF_2$, major isomer) and −121.66 and −122.68 (AB quartet, J=293 Hz, $CF_2$, minor isomer). IR (KBr pellet): 3428, 2969, 1693, 1632, 1526, 1221, 1200 $cm^{-1}$. MS ($DCI/CH_4$): m/z (rel intensity) 487 ($MH^+$, 45), 345 (10), 317 (15), 171 (100). HRMS ($C_{20}H_{31}F_5N_4O_4$) ($M^+$): calcd, 486.2265; obsd, 486.2256.

EXAMPLE 8

Preparation of N-(2-Furoyl)-L-valyl-N-[3,3,4,4,4-pentafluoro-1-(1-methylethyl)-2-oxobutyl]-L-prolinamide

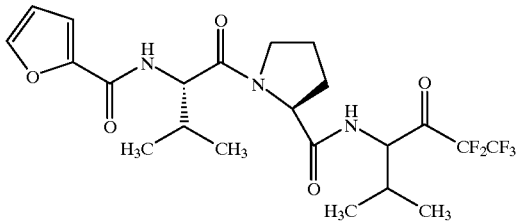

2-Furoyl chloride (143 mg, 1.11 mmol) was coupled with the product of Example 5 (e) (250 mg, 0.55 mmol) in the presence of NMM (112 mg, 1.11 mmol), according to the process described in Example 7. Purification by flash chromatography (3:1 EtOAc:hexane) gave 270 mg (95%) of the title compound (L-L-L) as a white solid. $^1$H NMR: δ7.50 (d, J=1.7, 0.8 Hz, 1H, NH), 7.47 (dd, J=1.7, 0.8 Hz, 1H, pyranyl), 7.12 (dd, J=3.5, 0.8 Hz, 1H, pyranyl), 6.96 (d, J=9.42 Hz, 1 H, NH), 6.50 (dd, J=3.6, 1.8 Hz, 1H, pyranyl), 4.96 (ddd, J=7.8, 4.2, 1.1 Hz, 1H, α-CH of Val), 4.61 (dd, J=8.0, 2.7 Hz, 1H, CH of Pro), 3.86 (m, 1H, NCH$_2$), 3.67 (m, 1H, CH$_2$), 1.04 (m, 9H, 3×CH$_3$), 0.90 (d, J=6.9 Hz, 3H, CH$_3$). $^{19}$F NMR: δ−82.08 (s, CF$_3$), −121.50 and −122.55 (AB quartet, J=293 Hz, CF$_2$). IR (KBr pellet): 3421, 3305, 2939, 1754, 1635, 1593, 1224, 1200 cm$^{-1}$. MS (DCI/CH$_4$): m/z (rel intensity) 510 (MH$^+$, 40), 317 (100). HRMS (C$_{22}$H$_{29}$F$_5$N$_3$O$_5$) (MH$^+$): calcd, 510.2027; obsd, 510.2025.

EXAMPLE 9

Preparation of N-[2-(4-Morpholinyl)ethanoyl]-L-valyl-N-[3,3,4,4,4-pentafluoro-1-(1-methylethyl)-2-oxobutyl]-L-prolinamide, Hydrochloride Salt

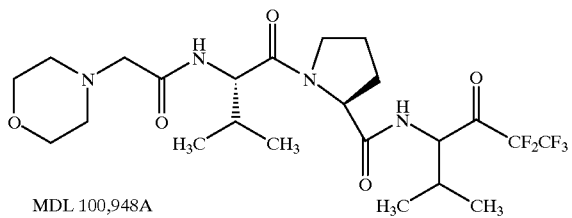

MDL 100,948A

•HCl a) Preparation of (4-Morpholinyl)acetic Acid, 1,1-Dimethylethyl Ester

To a stirred solution of tert-butyl bromoacetate (1.61 mL, 10.0 mmol) in THF (25 mL) was added morpholine (1.74 mL, 20.0 mmol); the resultant suspension was stirred for 1.5 h and then concentrated. The residue was dissolved in CH$_2$Cl$_2$ (50 mL)/saturated Na$_2$CO$_3$ (75 mL), the layers were separated, and the aqueous layer was extracted with additional CH$_2$Cl$_2$ (2×25 mL). The combined organics were washed with saturated Na$_2$CO$_3$ (20 mL) and brine (30 mL), dried and concentrated to give crude title compound. Trituration with EtOAc (15 mL), filtration, and concentration of the filtrate gave the title compound (2.01 g, 100%) as a colorless oil. TLC: R$_f$ 0.45 (EtOAc). $^1$H NMR: δ3.79–3.73 (m, 4H, CH$_2$OCH$_2$), 3.11 (s, 2H, CH$_2$), 2.61–2.55 (m, 4H, CH$_2$NCH$_2$), 1.46 (s, 9H, t-Bu). MS (DCI/CH$_4$): m/z (rel intensity) 202 (MH$^+$, 15), 201 (8), 200 (13), 174 (20), 146 (100), 100 (23). HRMS (C$_{10}$H$_{19}$NO$_3$) (MH$^+$): calcd, 201.1365; obsd, 201.1371.

b) Preparation of (4-Morpholinyl)acetic Acid, Trifluoroacetic Acid Salt

Trifluoroacetic acid (15 mL) was added to the compound of Example 9 (a) (1.00 g, 4.97 mmol); the solution was stirred fr 5 h and concentrated to give a yellow oil. Trituration with Et$_2$O (25 mL) gave the title compound (1.06 g, 82%) as an off-white solid. Mp: 118–121° C. $^1$H NMR (DMSO-d$_6$): δ4.06 (s, 2H, CH$_2$), 3.88–3.74 (m, 4H, CH$_2$OCH$_2$), 3.30–3.16 (m, 4H, CH$_2$NCH$_2$). $^{19}$F NMR (DMSO-d$_6$): δ−73.3 (s, CF$_3$). MS (DCI, CH$_4$): m/z (rel intensity) 146 (MH$^+$, 100), 115 (45), 100 (30). Anal. (C$_6$H$_{11}$NO$_3$.CF$_3$CO$_2$H): C, H, N.

c) Preparation of N-[2-(4-Morpholinyl)ethanoyl]-L-valyl-N-[3,3,4,4,4-pentafluoro-1-(1-methylethyl)-2-oxobutyl]-L-prolinamide, Hydrochloride Salt The acid of Example 9 (b) (260 mg, 1.0 mmol) was activated with oxalyl chloride (120 mg, 1.0 mmol) and coupled with the compound of Example 5 (e) (220 mg, 0.5 mmol) in the presence of NMM (300 mg, 3.0 mmol), as described in the method of Example 5 (h). Purification by flash chromatography (1:3 acetone:EtOAc) gave 189 mg (96%) of the title compound (3:2 L-L-L:L-L-D) as a white solid. The product was dissolved in diethyl ether, treated with HCl (gas) and solvent was removed in vacuo. $^1$H NMR: δ12.63 (br s, 1H, HCl), 8.92 (m, 1.3H, NH), 8.71 (d, J=8.7 Hz, 0.7H, NH), 8.20 (d, J=6.9 Hz, 1H, NH), 5.15 (m, 0.75H), 5.04 (m, 1.25H), 4.79 (m, 1H), 4.50 (m,2H), 1.14–0.90 (m, 12H, 4×CH$_3$). $^{19}$F NMR: δ−81.98 (s, CF$_3$, minor isomer), −82.16 (s, CF$_3$, major isomer), −120.49 and −123.29 (AB quartet, J=299 Hz, CF$_2$, minor isomer), −121.90 and −122.78 (AB quartet, J=296 Hz, CF$_2$, major isomer). IR (KBr pellet): 3430, 3280, 2971, 1754, 1685, 1629, 1449, 1224, 1200 cm$^{-1}$. MS (DCI/CH$_4$): m/z (rel intensity) 543 (MH$^+$, 100), 317 (10), 226 (10). Anal. (C$_{23}$H$_{35}$F$_5$N$_4$O$_5$.HCl.0.8H$_2$O): C, H, N.

EXAMPLE 10

Preparation of N-[3-(4-Morpholinyl)-1,3-dioxopropyl]-L-valyl-N-[3,3,4,4,4-pentafluoro-1-(1-methylethyl)-2-oxobutyl]-L-prolinamide

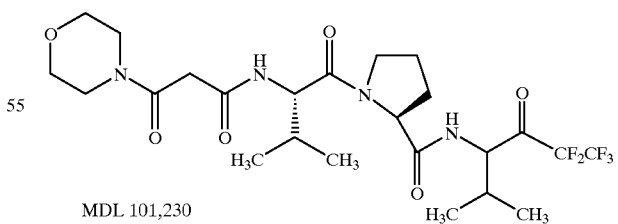

MDL 101,230 a) Preparation of 2-(4-Morpholinylcarbonyl)ethanoic Acid, Methyl Ester

To a solution of methyl malonyl chloride (10.0 g, 73.2 mmol) in CH$_2$Cl$_2$ (200 mL) at 0° C. was added rapidly dropwise a solution of morpholine (16.0 g, 0.183 mmol, 16.0 mL) in CH$_2$Cl$_2$ (50 mL), and the reaction mixture was stirred at room temperature for 4 h. The reaction mixture was filtered, the filtrate was diluted with additional CH$_2$Cl$_2$ (200 mL) and then washed successively with 1 N HCl, saturated NaHCO$_3$, and brine. The organics were concentrated to give a yellow oil which was purified by flash chromatography (EtOAc) to give 9.70 g (71%) of the title compound as a pale yellow oil. R$_f$ 0.28 (EtOAc). $^1$H NMR: δ3.76 (s, 3H), 3.72–3.62 (m, 6H), 3.49–3.43 (m, 4H). $^{13}$C NMR: δ167.81, 164.33, 66.61, 66.42, 52.46, 46.74, 42.22, 40.75. IR (neat): 1742, 1647, 1441. MS (EI): m/z (rel intensity) 187 (M$^+$, 28), 156 (M$^+$–OCH$_3$, 20), 144 (37), 114 (52), 101 (39), 86 (100). HRMS (C$_8$H$_{13}$NO$_4$) (MH$^+$): calcd, 188.0923; obsd, 188.0918.

b) Preparation of 2-(4-Morpholinylcarbonyl) ethanoic Acid

To a solution of the product of Example 10 (a) (1.70 g, 9.08 mmol) in MeOH (45 mL) was added 1 N LiOH (10 mL, 9.99 mmol), and the reaction mixture was stirred at room temperature for 2.5 h. The pH was adjusted to 3 with 1 N HCl and the solvent removed in vacuo. Recrystallization from CH$_3$CN gave 0.216 g (14%) of the title compound as a white solid. $^1$H NMR: δ13.17–12.32 (very br s, 1H), 3.61–3.51 (m, 4H), 3.50–3.36 (m, 4H), 3.45 (s, 2H). $^{13}$C NMR: δ16914, 165.09, 65.96, 46.15, 41.62, 40.62. MS (EI): m/z (rel intensity) 173 (M$^+$, 18), 129 (M$^+$–CO$_2$, 53), 86 (77), 57 (100). HRMS (C$_7$H$_{11}$NO$_4$) (MH$^+$): calcd. 174.0766: obsd, 174.0765.

c) Preparation of N-[3-(4-Morpholinyl)-1,3-dioxopropyl]-L-valyl-N-[3,3,4,4,4-pentafluoro-1-(1-methylethyl)-2-oxobutyl]-L-prolinamide The acid of Example 10 (b) (561 mg, 3.24 mmol) was activated with oxalyl chloride (400 mg, 3.17 mmol) and coupled with the compound of Example 5 (e) (500 mg, 3.17 mmol) in the presence of NMM (980 mg, 9.70 mmol) as described in the method of Example 5 (h). Purification by flash chromatography (1:3 acetone:EtOAc) gave 475 mg (75%) of the title compound (2:1 L-L-L:L-L-D) as a white solid.

$^1$H NMR: δ8.03 (m, 1H, NH), 7.97 (d, J=7.6 Hz, 0.33H, NH), 7.62 (d, J=7.7 Hz, 0.67H, NH), 4.93 (m, 1H, α-CH of Val), 4.72 (dd, J=8.0, 2.0 Hz, 0.33H, CH of Pro), 4.63 (dd, J=8.0, 2.7 Hz, 0.67H, α-CH of Pro), 4.58 (dd, J=8.3, 7.2 Hz, 1H, CH of Val), 3.86–3.42 (m, 10H, 2×NCH$_2$CH$_2$O and NCH$_2$ of Pro), 3.36 (s, 2H, CH$_2$), 2.54–1.75 (series of m, 6H, 2×β-CH of Val and CH$_2$CH$_2$), 1.09–0.87 (m, 12H, 4×CH$_3$). $^{19}$F NMR: δ–82.17 (s, CF$_3$, major isomer), –88.21 (s, CF$_3$, minor isomer), –121.64 and –122.61 (AB quartet, J=298 Hz, CF$_2$, major isomer), –121.59 and –122.72 (AB quartet, J=293 Hz, CF$_2$, minor isomer). IR (KBr pellet): 3301, 2969, 1753, 1628, 1531, 1444, 1224, 1199, 1116 cm$^{-1}$. MS (DCI/CH$_4$): m/z (rel intensity) 571 (MH$^+$, 100), 317 (75), 255 (20, 228 (18). HRMS (C$_{24}$H$_{35}$F$_5$N$_4$O$_6$) (MH$^+$): calcd, 570.2476; obsd, 570.2455.

EXAMPLE 11

Preparation of N-[[6-(4-Morpholinylcarbonyl)pyrid-3-yl]carbonyl-L-valyl-N-[3,3,4,4,4-pentafluoro-1-(1-methylethyl)-2-oxobutyl]-L-prolinamide

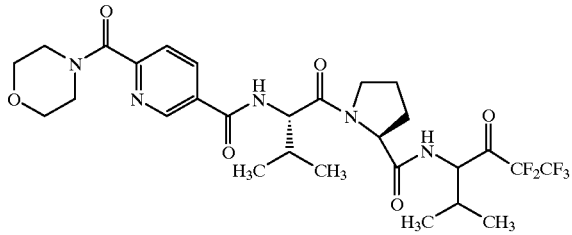

a) Preparation of Pyridine -2,5-dicaboxylic Acid, 5-tert-Butyl Ester, 2-Methyl Ester To a solution of 2-tert-butyl-1,3-dicyclohexyl isourea (5.63 g, 20.1 mmol) in CH$_2$Cl$_2$ (20 mL) at 5° C. was added a compound of the formula

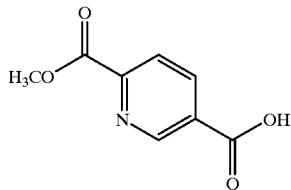

(Isagawa, K. et al., *Nippon Kagaku Zasshi* (1967) 88, 553–556), (1.49 g, 8.24 mmol) in several portions. After 15 min, the cooling bath was removed. As the reaction mixture began to warm, a precipitate formed and the reaction temperature rose above 25° C. The reaction mixture was cooled to room temperature and CH$_2$Cl$_2$ (5 mL) was added to aid stirring. After stirring overnight, the mixture was diluted with CH$_2$Cl$_2$ (30 mL) and filtered and the pale blue-green solid washed with CH$_2$Cl$_2$. The combined filtrates were diluted with ether, washed with dilute NaHCO$_3$, and concentrated. The residue was purified by flash chromatography (55:45 cyclohexane:EtOAc) to give 1.01 g (52%) of the title compound as a white solid. A portion of the material was recrystallized (ether/pentane) to give analytically pure sample. Mp: 111–112° C. $^1$H NMR: δ9.26 (d, J=2.1 Hz, 1H), 8.39 (dd, J=8.1, 2.1 Hz, 1H), 8.19 (dd, J=8.1, 0.7 Hz, 1H), 4.04 (s, 3H), 1.63 (s, 9H). IR (KBr): 3420, 2984, 1711, 1379, 1310, 1290, 1246, 1134, 1126, 746 cm$^{-1}$. MS (EI): m/z (rel intensity) 238 (M+1), 237 (M$^+$), 182, 179, 164, 57 (100). Anal. (C$_{12}$H$_{15}$NO$_4$): C, H, N.

b) Preparation of 6-(4-Morpholinylcarbonyl) nicotinic Acid, tert-Butyl Ester

A solution of the compound of Example 11 (a) (0.935 g, 3.4 mmol) and morpholine (3.96 g, 46.0 mmol, 3.98 mL) in THF (6 mL) was refluxed for 3 days. The reaction mixture was concentrated; the residue was dissolved in EtOAc, washed with H$_2$O (2×), and concentrated to give 1.01 g of a ligh-yellow solid. Recrystallization (ether/pentane, 2×) gave 0.542 g (47%) of the title compound as a pale cream solid. Mp: 91–93° C. $^1$H NMR: δ9.13 (dd, J=2.1, 1.0 Hz, 1H), 8.36 (dd, J=8.1, 2.1 Hz, 1H), 7.75 (dd, J=8.1, 0.9 Hz, 1H), 3.83 (s, 4H), 3.73–3.55 (m, 4H), 1.62 (s, 9H). IR (KBr):

2984, 2965, 1707, 1634, 1370, 1317, 1287, 1169, 1132, 117 cm$^{-1}$. MS (DCI/CH$_4$): m/z (rel intensity) 293 (MH$^+$), 292, 123, 86 (100). Anal. (C$_{15}$H$_{20}$N$_2$O$_4$): C, H, N.

c) Preparation of 6-(4-Morpholinylcarbonyl) nicotinic Acid

Into a solution of the compound of Example 11 (b) (0.606 g, 2.07 mmol) in CH$_3$NO$_2$ (5 mL) was bubbled HCl(g) for 20 min. After standing for 20 min, the solvent was removed in vacuo to give a pale yellow solid. Recrystallization (acetone) gave 0.335 g (68%) of the title compound as a white solid. Mp: 181–183° C. $^1$H NMR (CD$_3$OD): δ9.26 (d, J=1.1 Hz, 1H), 8.78 (dd, J=8.1 Hz, 1H), 3.80 (s, 4H), 3.67 (m, 2H), 3.51 (m, 2H). IR (KBr): 2928, 2872, 1717, 1601, 1285, 1262, 1111 cm$^{-1}$. MS (DCI/CH$_4$): m/z (rel intensity) 277 (M +C$_3$H$_7^+$), 265 (M+C$_2$H$_5^+$), 238, 237 (MH$^+$, 100). Anal. (C$_{11}$H$_{12}$N$_2$O$_4$): C, H, N.

d) Preparation of N-[[6-(4-Morpholinylcarbonyl) pyrid-3-yl]carbonyl]-L-valyl-N-[3,3,4,4,4-pentafluoro-1-(1-methylethyl)-2-oxobutyl]-L-prolinamide The acid of Example 11 (d) (0.200 g, 0.847 mmol) was activated with thionyl chloride (0.101 g, 0.847 mmol, 61.5 μL) and benzyltriethylammonium chloride (trace) in dichloroethane (1.6 mL) and coupled with the compound of Example 5 (e) (0.383 g, 0.847 mmol) in the presence of NMM (0.343 g, 3.39 mmol, 0.372 mL) in CH$_2$Cl$_2$ (10 mL), according to the method described in Example 6. Purification by flash chromatography (1:9 acetone:EtOAc) gave 0.375 g (70%) of the title compound (1.5:1 L-L-L:L-L-D) as a white foam. TLC: R$_f$ 0.40 (3:7 acetone:EtOAc). $^1$H NMR: δ9.05 (d, J=1.8 Hz, 1H, aryl), 8.21 (dd, J=8.1, 1.0 Hz, 1H, aryl), 7.88 (d, J=7.8 Hz, 0.4H, NH), 7.74 (dd, J=8.0, 2.3 Hz, 1H, aryl), 7.46 (d, J=8.0 Hz, 0.6H, NH), 7.29 (d, J=8.9 Hz, 0.6H, NH), 7.25 (d, J=8.8 Hz, 0.4H, NH), 5.03–4.96 (m, 1H, α-CH of Val), 4.82 (dd, J=8.6, 7.3 Hz, 1H, α-CH of Val), 4.65 (dd, J=7.9, 2.3 Hz, 0.4H, α-CH of Pro), 4.56 (dd, J=7.8, 3.0 Hz, 0.6H, α-CH of Pro), 3.97–3.57 (series of m 10H, 2×OCH$_2$CH$_2$N and CH$_2$N of Pro), 2.49–1.84 (m, 6H, CH$_2$CH$_2$ of Pro and 2×β-CH of Val), 1.12–0.85 (m, 12H, 4×CH$_3$). $^{19}$F NMR: δ-82.12 (s, CF$_3$, major), -82.15 (s, CF$_3$, minor), -121.46 and -122.78 (AB quartet, J=296 Hz, CF$_2$, minor), -121.82 and -122.58 (AB quartet, J=296 Hz, CF$_2$, major). MS (DCI/CH$_4$): m/z (rel intensity) 634 (MH$^+$, 27), 317 (100). Anal. (C$_{28}$H$_{36}$F$_5$N$_5$O$_6$·0.3H$_2$O): C, H, N.

EXAMPLE 12
Preparation of N-[4-[(4-Morpholinylcarbonyl) amino]benzoyl]-L-valyl-N-[3,3,4,4,4-pentafluoro-1-(1-methylethyl)-2-oxobutyl]-L-prolinamide

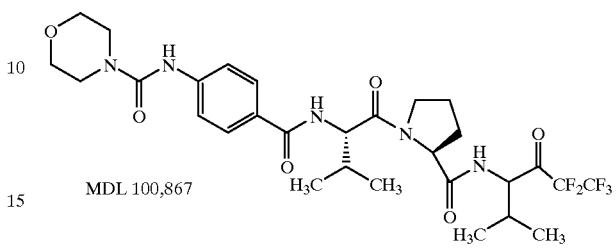

MDL 100,867 a) Preparation of 4-[(4-Morpholinylcarbonyl)amino] benzoic Acid, Ethyl Ester To a solution of morpholine (0.684 g, 7.85 mmol, 0.687 mL) in toluene (8 mL) was added dropwise ethyl 4-isocyanatobenzoate (1.50 g, 7.85 mmol) in toluene (8 mL). After stirring for 18 h at room temperature, the precipitate was filtered, washed with cold toluene, and dried under vacuum to give 2.00 g (91%) of the title compound as a white solid. $^1$H NMR: δ7.96 (d, J=8.8 Hz, 2H, aryl), 7.45 (d, J=8.8 Hz, 2H, aryl), 6.80 (br s, 1H, NH), 4.35 (q, J=7.1 Hz, 2H, CO$_2$CH$_2$), 3.75–3.70 (m, 4H, CH$_2$OCH$_2$), 3.53–3.47 (m, 4H, CH$_2$NCH$_2$), 1.38 (t, J=7.1 Hz, 3H, CH$_3$). $^{13}$C NMR: δ166.3, 154.4, 143.2, 130.7, 124.7, 118.5, 66.4, 60.8, 44.3, 14.3. IR (KBr): 3328, 1716, 1645, 1592, 1526, 1423, 1308, 1279, 1247 cm$^{-1}$. MS (DCI/CH$_4$): m/z (rel intensity) 307 (M+C$_2$H$_5^+$, 39), 279 (MH$^+$, 100). Anal. (C$_{14}$H$_{18}$N$_2$O$_4$): C, H, N.

b) Preparation of 4-[(4-Morpholinylcarbonyl)amino] benzoic Acid

To a solution of the compound of Example 12 (a) (0.823 g, 2.96 mmol) in MeOH (15 mL) was added 1 N LiOH (3.25 mL, 3.25 mmol), and the reaction mixture was stirred at room temperature for 18 h. The MeOH was removed in vacuo and the aqueous residue acidified with concentrated HCl. After 1 h at 0° C., the precipitate was collected, washed with H$_2$O, and dried under vacuum over KOH to give 0.281 g (38%) of the title compound as a fluffy white powder. $^1$H NMR: δ13.51–11.37 (very br s, 1H, CO$_2$H), 8.88 (s, 1H, NH), 7.86–7.80 (m, 2H, aryl), 7.62–7.56 (m, 2H, aryl), 3.64–3.59 (m, 4H, CH$_2$OCH$_2$), 3.48–3.43 (m, 4H, CH$_2$NCH$_2$). $^{13}$C NMR: δ167.13, 154.66, 144.79, 130.05, 123.63, 118.25, 65.96, 44.22. MS (DCI/CH$_4$): m/z (rel intensity) 250 (M$^+$, 31), 114 (100), 70 (77). HRMS (C$_{12}$H$_{14}$N$_2$O$_4$) (MH$^+$): calcd, 251.1032; obsd, 251.1039.

c) Preparation of N-[4-[(4-Morpholinylcarbonyl) amino]benzoyl]-L-valyl-N-[3,3,4,4,4-pentafluoro-1-(1-methylethyl)-2-oxobutyl]-L-prolinamide The acid of Example 12 (b) (400 mg, 1.60 mmol) was activated with oxalyl chloride (201 mg, 1.60 mmol) and coupled with the product of Example 5 (e) (250 mg, 0.55 mmol) in the presence of NMM (380 mg, 3.75 mmol) as described in the method disclosed in Example 5 (h). Purification by flash chromatography (3:7 EtOAc:hexane) gave 295 mg (82%) of the title compound (4:1 L-L-L:L-L-D) as a white solid. $^1$H NMR: δ7.91 (d, J=7.9 Hz, 0.2H, NH), 7.74 (d, J=8.7 Hz, 0.2H, NH), 7.72 (d, J=8.7 Hz, 2H, aryl), 7.54 (d, J=8.0 Hz, 0.8H, NH), 7.43 (d, J=8.7 Hz, 2H, aryl), 6.88 (d, J=8.7 Hz, 0.8H, NH), 6.82 (s, 1H, NH), 4.97 (dd, J=7.8, 4.8 Hz, 1H, α-CH of Val), 4.80 (dd, J=8.7, 7.0 Hz, 1H, α-CH of Val), 4.70 (dd, J=7.8, 2.8 Hz, 0.2H, α-CH of Pro), 4.61 (dd, J=7.8, 2.8 Hz, 0.8H, CH of Pro), 3.86 (m, 1H, NCH$_2$ of Pro), 3.73 (m, 4H, CH$_2$OCH$_2$), 3.67 (m, 1H, NCH$_2$ of Pro), 3.50 (m, 4H, CH$_2$NCH$_2$), 2.51–0.75 (series of 6H, 2×β-CH of Val and CH$_2$CH$_2$), 1.11–1.00 (m, 9H, 3×CH$_3$), 0.87 (d, J=6.9 Hz, 3H, CH$_3$). $^{19}$F NMR: δ−82.16 (s, CF$_3$, major isomer), −82.19 (s, CF$_3$, minor isomer), −121.72 and −122.59 (AB quartet, J=293 Hz, CF$_2$, major isomer), −121.75 and −122.26 (AB quartet, J=293 Hz, CF$_2$, minor isomer). IR (KBr pellet): 3328, 2969, 1753, 1635, 1522, 1442, 1312, 1240, 1198 cm$^{-1}$. MS (DCI/CH$_4$): m/z (rel intensity) 648 (MH$^+$, 30), 598 (38), 561 (90), 317 (100). HRMS (C$_{29}$H$_{39}$F$_5$N$_5$O$_3$) (MH$^+$): Calcd, 648.2820; Obsd, 648.2812.

EXAMPLE 13

Preparation of N-[4-[[Methyl[2-(4-morpholinyl) ethyl]amino]-carbonyl]benzoyl]-L-valyl-N-[3,3,4,4, 4-pentafluoro-1-(1-methylethyl)-2-oxobutyl]-L-prolinamide

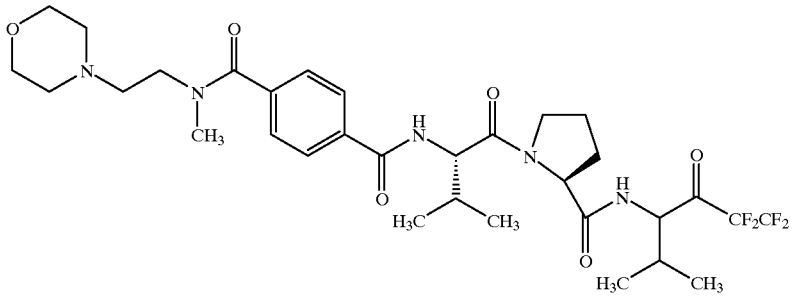

a) Preparation of N-[4-[(1,1-Dimethylethoxy) carbonyl]-benzoyl]-L-valyl-N-[3,3,4,4,4-pentafluoro-1-(1-methylethyl)-2-oxobutyl]-L-prolinamide Hydrogen tert-butyl pthalate (Buckle, D. R., et al., *J. Chem. Soc. C* 1971, 2821–2823) was activated with IBCF (0.41 g, 3.0 mmol) and NMM (0.91 g, 3.0 mmol) and coupled with the compound of Example 5 (e) (1.2 g, 2.6 mmol), as described in the method disclosed in Example 3. Purification by flash chromatography (1:3 EtOAc:hexane) gave 1.10 g (55%) of the title compound (1:1 L-L-L:L-L-D) as a white solid. $^1$H NMR: δ8.05 (d, J=2.5 Hz, 1H, 0.5 of 2CH aryl), 8.02 (d, J=2.5 Hz, 1H, 0.5 of 2CH aryl), 7.85 (d, J=5.4 Hz, 1H, 0.5 of 2CH aryl), 7.84 (overlapped, 0.5H, NH), 7.82 (d, J=5.4 Hz, 1H, CH of aryl), 7.47 (d, J=7.8 Hz, 0.5H, NH), 6.95 (m, 1H, NH), 4.99 (m, 1H, α-CH of Val), 4.84 (m, 1H, α-CH of Val), 4.75 (dd, J=8.0, 2.1 Hz, 0.5H, CH of Pro), 4.63 (dd, J=8.0, 2.9 Hz, 0.5H, CH of Pro), 3.89 (m, 1H, NCH$_2$), 3.70 (m, 1H, NCH$_2$), 2.51–1.85 (series of m, 6H, 2×β-CH of Val and CH$_2$CH$_2$), 1.66 [s, 4.5H, 0.5 of C(CH$_3$)$_3$], 1.63 [s, 4.5H, 0.5 of C(CH$_3$)$_3$], 1.06 (m, 9H, 3×CH$_3$), 0.88 (d, J=6.9 Hz, 3H, CH$_3$). $^{19}$F NMR: δ−82.13 (s, CF$_3$, isomer I), −82.17 (s, CF$_3$, isomer II), −121.54 and −122.63 (AB quartet, J=296 Hz, CF$_2$, isomer I), −121.57 and −122.66 (AB quartet, J=287 Hz, CF$_2$, isomer II). IR (KBr pellet): 3425, 3325, 2974, 1755, 1715, 1695, 1631, 1529, 1224, 1199 cm$^{-1}$. MS (DCI/CH$_4$): m/z (rel intensity) 620 (MH$^+$, 78), 564 (24), 544 (20), 516 (99), 317 (00). HRMS (C$_{29}$H$_{38}$F$_5$N$_3$O$_6$) (M$^+$): calcd 619.2681; obsd, 619.2667.

b) Preparation of N-(4-Carboxybenzoyl)-L-valyl-N-[3,3,4,4,4-pentafluoro-1-(1-methylethyl)-2-oxobutyl]-L-prolinamide A solution of the compound of Example 13 (a) (750 mg, 1.21 mmol) in ethyl acetate (300 mL) was cooled to −5° C. and treated with HCl (gas) until saturation. The mixture was stirred at −5° C. for 3 h, the solvent was removed in vacuo, and the crude residue was redissolved in EtOAc. The organic phase was extracted with dilute NaHCO$_3$. The NaHCO$_3$ extract was acidified with KHSO$_4$, and the producted was extracted with diethyl ether. Removal of solvent gave 400 mg (64%) of the title compound (3:2 L-L-L:L-L-D) as a white solid. $^1$H NMR: δ8.09 (d, J=8.6 Hz, 0.5H, NH), 8.03 (d, J=8.6 Hz, 0.5H, NH), 7.98 (d, J=8.1 Hz, 2H, CH aryl), 7.89 (d, J=8.1 Hz, 2H, CH aryl), 7.64 (d, J=7.8 Hz, 0.5H, NH), 7.06 (d, J=7.2 Hz, 0.5H, NH), 5.02 (m, 1H, α-CH of Val), 4.77 (m, 1.5H, α-CH of Val and 0.5 of CH of Pro), 4.63 (m, 0.5H, CH of Pro), 4.12 (m, 1H, CH$_2$ of Pro), 3.77 (m, 1H, CH$_2$ of Pro), 2.52–1.88 (series of m, 6H, 2×β-CH of Val and CH$_2$CH$_2$), 1.11 (m, 9H, 3×CH$_3$), 0.89 (m, 3H, CH$_3$). $^{19}$F NMR: δ−82.11 (s, CF$_3$, major isomer), −82.14 s, CF$_3$, minor isomer), −121.54 and −122.57 (AB quartet, J=293 Hz, CF$_2$, major isomer), −121.43 and −122.80 (AB quartet, J=296 Hz, CF$_2$, minor isomer). IR (KBr pellet): 3425, 3313, 2941, 1753, 1697, 1631, 1529, 1224 cm$^{-1}$. MS (DCI/CH$_4$): m/z (rel intensity) 564 (MH$^+$, 45), 317 (100). HRMS (C$_{23}$H$_{31}$F$_5$N$_3$O$_6$) (MH$^+$): calcd, 564.2133; obsd, 564.2125.

c) Preparation of N-[4-[[Methyl[2-(4-morpholinyl) ethyl]amino]-carbonyl]benzoyl]-L-valyl-N-[3,3,4,4, 4-pentafluoro-1-(1-methylethyl)-2-oxobutyl]-L-prolinamide The acid of Example 13 (b) (0.36 g, 0.64 mmol) was activated with oxalyl chloride (0.07 mL, 0.83 mmol) and DMF (3 drops) and coupled with 4-[2-(methylamino)ethyl]- morpholine (92 mg, 0.64 mmol) using NMM (0.14 mL, 1.28 mmol) according to the method described in Example 5 (h). Purification by flash chromatography (75:25 acetone:EtOAc) gave 0.25 g (57%) of the title compound (7:1 L-L-L:L-L-D) as an off-white foam. TLC: $R_f$ 0.19 (3:1 acetone:EtOAc). $^1$H NMR (partial): δ7.88–7.82 and 7.52–7.46 (pr m, 4H, aryl), 7.42 (br d, J=7.6 Hz, 1H, NH), 6.84 (br d, J=8.8 Hz, 1H, NH), 5.02–4.96 (m, 1H, CH), 4.85 (dd, J=8.6, 7.0 Hz, 1H, CH), 4.72 (dd, J=8.0, 2.0 Hz, 1/8H, CH of Pro), 4.6 (dd, J=8.1, 2.9 Hz, 7/8H, CH of Pro), 1.14–0.82 (m, 12H, 4×CH$_3$). $^{19}$F NMR: δ–82.12 (s, CF$_3$, major isomer), –82.15 (s, CF$_3$, minor isomer), –121.52 and –122.70 (AB quartet, J=294 Hz, CF$_2$, minor isomer), –121.54 and –122.58 (AB quartet, J=294 Hz, CF$_2$, major isomer). MS (DCI/CH$_4$): m/z (rel intensity) 691 (26), 690 (MH$^+$, 100), 374 (62), 317 (18), 113 (22), 100 (43), 84 (36), 83 (23). HRMS (C$_{32}$H$_{45}$F$_5$N$_5$O$_6$) (MH$^+$): calcd, 690.3290; obsd, 690.3274.

EXAMPLE 14

Preparation of N-[4-[[4-(4-Morpholinylcarbonyl)-1-piperazinyl]carbonyl]benzoyl]-L-valyl-N-[3,3,4,4,4-pentafluoro-1-(1-methylethyl)-2-oxobutyl]-L-prolinamide c) Preparation of 4-[[4-(4-Morpholinylcarbonyl)-1-piperazinyl]carbonyl]benzoic Acid, Methyl Ester To a stirred suspension of monomethyl terephthalate (0.40 g, 2.20 mmol) in CH$_2$Cl$_2$ (10 mL) and DMF (0.2 mL) was added oxalyl chloride (0.19 mL, 2.20 mmol) dropwise. NOTE: VIGOROUS GAS EVOLUTION. After cessation of gas evolution, the reaction mixture was stirred for 45 min and then concentratd to give the corresponding acid chloride as a white solid. The acid chloride, without further purification, was dissolved in CH$_2$Cl$_2$ (15 mL) and a solution of the compound of Example of 14 (b) (0.94 g, 2.20 mmol) and NMM (0.97 mL, 8.80 mmol) in CH$_2$Cl$_2$ (5 mL) added. After 2.5 h, the reaction mixture was diluted with CH$_2$Cl$_2$ (40 mL) and washed with 1.0 N HCl (2×35 mL), saturated NaHCO$_3$ (2×25 mL), and brine (25 mL). Drying and concentration gave crude title compound. Flash chromatography (4×12 cm) eluting with acetone/EtOAc (15:85) gave the title compound (0.53 g, 66%) as a white solid. TLC: $R_f$ 0.20 (3:7 acetone:EtOAc). $^1$H NMR (DMSO-d$_6$): δ8.04–7.97 and 7.57–7.51 (pr m, 4H, aryl), 3.87 (s, 3H, OCH$_3$), 3.67–3.57 (m, 2H, CH$_2$N), 3.54 (t, J=4 Hz, 4H,

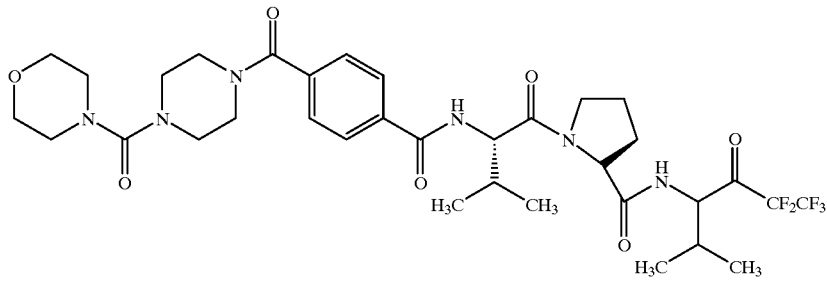

CH$_2$OCH$_2$), 3.32–3.19 and 3.17–3.10 (pr m, 6H, 3×CH$_2$N), 3.13 (t, J=4 Hz, 4H, CH$_2$NCH$_2$). MS (EI): m/z (rel intensity) 361 IM$^+$, 12), 330 (8), 231 (22), 163 (100), 114 (71), 70 (41). HRMS (C$_{18}$H$_{24}$N$_3$O$_5$) (MH$^+$): calcd, 362.1716; obsd, 362.1707.

d) Preparation of 4-[[4-(4-Morpholinylcarbonyl)-1-piperazinyl]carbonyl]benzoic Acid To a stirred solution of the compound of Example 14 (c) (0.52 g, 1.44 mmol) in CH$_3$OH (10 mL) and CH$_3$CN (8 mL) were added 1.0 N LiOH (1.7 mL, 1.7 mmol) and water (4 mL). After 18 h, the reaction mixture was concentrated to remove CH$_3$OH and CH$_3$CN, and the alkaline aqueous solution was adjusted to pH 3 using 1.0 N HCl. After the solution was cooled, a white solid (0.43 g), crude title compound was collected by filtration. The solid was stirred with CH$_2$Cl$_2$ (40 mL) for 20 min, Na$_2$SO$_4$ was added and the mixture was filtered. Addition of hexane to the filtrate and concentration gave the title compound (0.29 g, 58%) as a white solid. Mp: 203–205° C. $^1$H NMR: δ8.20–8.13 and 7.54–7.47 (pr m, 4H, aryl), 3.90–3.74 (m, 2H, CH$_2$N), 3.70 (t, J=4.4 Hz, 4H, CH$_2$OCH$_2$), 3.52–3.18 (m, 6H, 3×CH$_2$N), 3.32 (t, J=4.4 Hz, 4H, CH$_2$NCH$_2$). MS (DCI, CH$_4$): m/z (rel intensity) 349 (20), 348 (MH$^+$, 100), 217 (15). HRMS (C$_{17}$H$_{22}$N$_3$O$_5$) (MH$^+$): calcd, 348.1559; obsd, 348.1548.

a) Preparation of 4-(4-Morpholinylcarbonyl)-1-piperazinecarboxylic Acid, 1,1-Dimethylethyl Ester To a stirred solution of tert-butyl 1-piperazinecarboxylate (2.50 g, 13.42 mmol) in CH$_2$Cl$_2$ (75 mL) cooled in an ice-water bath was added 4-morpholinecarbonyl chloride (1.57 mL, 13.42 mmol) followed by Et$_3$N (3.74 mL, 26.84 mmol), and the reaction mixture was allowed to warm to room temperature. After 15 h, the reaction mixture was washed with 1.0 N HCl (50 mL), saturated NaHCO$_3$ (75 mL), and brie (50 mL), dried, and concentrated to give the title compound (3.80 g, 95%) as a white solid. Mp: 171–173° C. $^1$H NMR: δ3.69 (t, J=4.9 Hz, 4H, CH$_2$OCH$_2$), 3.46–3.40 (m, 4H, CH$_2$NCH$_2$), 3.28 (t, J=4.9 Hz, 4H, CH$_2$NCH$_2$), 3.25–3.20 (m, 4H, CH$_2$CH$_2$), 1.47 (s, 9H, t-Bu). MS (DCI/CH$_4$): m/z (rel itensity) 300 (MH$^+$, 73), 272 (28), 244 (100), 200 (73). Anal. (C$_{14}$H$_{25}$N$_3$O$_4$): C, H, N.

b) Preparation of 4-(1-Piperazinylcarbonyl) morpholine, Bis(trifluoroacetic acid salt)

Trifluoroacetic acid (10 mL) was added to the compound of Example 14 a) (1.50 g, 5.01 mmol); the solution was stirred for 30 min and then concentrated to give an oil. Trituration with Et$_2$O (15 mL) and filtration gave the title compound (2.02 g, 94%) as a white solid. $^1$H NMR (DMSO-d$_6$): δ8.91 (br s, 2H), 8.20 (br s, 1H), 3.53 (t, J=4 Hz, e) Preparation of N-[4-[[4-(4-Morpholinylcarbonyl)-1-piperazinyl]carbonyl]benzoyl]-L-valyl-N-[3,3,4,4,4-pentafluoro-1-(1-methylethyl)-2-oxobutyl]-L-prolinamide The acid of Example 14 (d) (230 mg, 0.66 mmol) was activated with oxalyl chloride (64 μL, 0.73 mmol) and DMF (2 drops) and coupled with the product of Example 5 (e) (299 mg, 0.66 mmol) using NMM 90.22 mL, 1.99 mmol) as described in the method of Example 5 (h). Purification by flash chromatography (45:55 acetone:EtOAc) gave 366 mg (74%) of the title compound (9:1 L-L-L:L-L-D) as a white solid. TLC: $R_f$ 0.33 (1:1 acetone:EtOAc). $^1$H NMR: δ7.87 and 7.48 (pr br d, J=7.3 Hz, 4H, aryl), 7.39 (br d, J=7.8 Hz, 1H, NH), 6.89 (br d, J=8.5 Hz, 1H, NH), 4.99 (dd, J=7.6, 4.2 Hz, 1H, α-CH), 4.85 (t, J=7.5 Hz, 1H, α-CH of Val), 4.71 (d, J=7.3 Hz, 0.1H, CH of Pro), 4.61 (dd, J=7.7, 2.4 Hz, 0.9H, CH of Pro), 3.98–3.59 and 3.59–3.15 (pr m, 18H), 2.56–1.84 (m, 6H, 2×β-CH of Val and $CH_2CH_2$), 1.14–0.82 (m, 12H, 4×$CH_3$). $^{19}$F NMR: δ−82.11 (s, $CF_3$, major isomer), −82.15 (s, $CF_3$, minor isomer), −121.50 and −122.70 (AB quartet, J=297 Hz, $CF_2$, minor isomer), −121.54 and −122.58 (AB quartet, J=297 Hz, $CF_2$, major isomer). MS ($DCI/CH_4$): m/z (rel intensity) 745 ($MH^+$, 100), 547 (15), 317 (55), 169 (16). Anal. ($C_{34}H_{45}F_5N_6O_7$): C., H, N.

EXAMPLE 15

Preparation of N-[4-(4-Morpholinylcarbonyl)benzoyl]-L-valyl-N-[3,3,4,4,4-pentafluoro-1-(1-methylethyl)-2-oxobutyl]-D,L-1,2,3,4-tetrahydro-3-isoquinolinamide

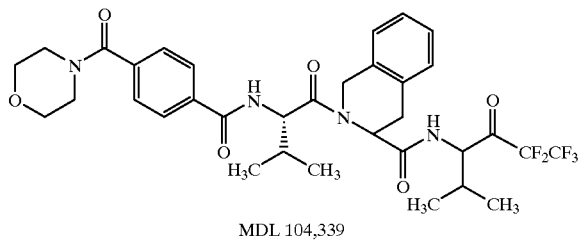

MDL 104,339 a) Preparation of N-[(1,1-Dimethylethoxy)carbonyl]-L-valyl-succinimide

To a cooled (icebath) stirred solution of BOC-L-valine (4.56 g, 0.021 mol), and N-hydroxysuccinimide (2.41 g, 0.021 mol) in DME (50 mL) was added DCC (4.75 g, 0.023 mol). The reaction was stirred for 6 h at 5° C. and then left to stand in the refrigerator over night. The reaction was then cold filtered, washing with $Et_2O$, and conc to yield a solid which was crystallized from EtOAc/hexane to give the desired product as a white crystalline sold (4.59 g, 69.5%): mp 123–124° C.; $^1$H NMR (300 MHz, $CDCl_3$) δ5.00–4.95 (d, 1H, J=9.3 Hz), 4.62 (dd, 1H, J=4.97 Hz), 2.85 (s, 4H), 2.75–2.44 (m, 1H), 1.45 (s, 9H), 1.25–0.90 (m, 6H); $^{13}$C NMR ($CDCl_3$) δ168.6, 167.9, 155.1, 155.0, 80.4, 77.4, 77.2, 77.0, 76.6, 76.5, 57.0, 31.6, 31.1, 28.2, 28.1, 28.0, 27.99, 27.93, 25.5, 18.6, 17.3; MS ($Cl/CH_4$) m/z 315 ($MH^+$), 299, 287, 259, 241, 215 (base peak), 173, 172, 145, 144, 116, 100, 72. Anal. Calcd. for $C_{14}H_{22}N_2O_6$: C, 53.49; H, 7.05; N, 8.91. Found: C, 53.67; H, 7.06; N, 8.81.

b) Preparation of N-[(1,1-dimethylethoxy)carbonyl]-L-valyl-D,L-1,2,3,4-tetrahydro-3-isoquinoline carboxylic acid To a stirred solution of 1,2,3,4-tetrahydro-3-isoquinoline carboxylic acid hydrochloride salt (2.1 g, 10 mmol) and $Et_3N$ (3.0 mL, 20 mmol) in DMF (40 mL) was added the product of example 15 (a) (2.0 g, 6 mmol) and the reaction was heated to 105° C. for 2 h. Upon cooling, the reaction was conc in vacuo and the oily residue was dissolved in EtOAc and washed with 3N HCl (2×30 mL), dried ($Na_2SO_4$) and conc. The crude was chromatographed (eluted with 1:27 $MeOH/CH_2Cl_2$) to give the desired compound (484 mg, 13%) as an isomeric mixture white foam; $^1$H NMR (300 MHz, $CDCl_3$) δ7.2 (m, 4H); 5.6 (d, 0.25H, J=8 Hz, NH), 5.4 (d, 0.75H, J=8 Hz, NH), 5.38 (m, 1H), 5.1–4.4 (series of m, 3H), 3.5–3.05 (series of m, 2H), 2.08 and 1.93 (pr of m, 1H, ratio 2:1, L/D), 1.4 (s, 9H, tBu), 1.1–0.8 (m, 6H, 2×$CH_3$).

c) Preparation of N-[(1,1-dimethylethoxy)carbonyl]-L-valyl-N-[3,3,4,4,4-pentafluoro-1-(1-methylethyl)-2-oxobutyl]-D,L-1,2,3,4-tetrahydro-3-isoquinolinamide To a stirred solution of the product of example 15 (b) (450 mg, 1.2 mmol) and NMM (0.13 mL, 1.2 mmol) in dry $CH_2Cl_2$ (30 mL) at −20° C. under nitrogen was added dropwise isobutylchloroformate (0.16 mL, 1.2 mmol). After 20 min, 4-amino-1,1,1,2,2-pentafluoro-5-methyl-3-hexanone hydrochloride (306 mg, 1.2 mmol) was added, immediately followed by another equivalent of NMM (0.13 mL, 1.2 mmol). The reaction mixture was stirred at −20° C. for 1 h, then allowed to warm to room temperature and poured into cold, dilute HCl and extracted with $CH_2Cl_2$. The organic extract as washed with water, dilute aqueous $NaHCO_3$, brine and dried ($MgSO_4$). Concentration in vacuo to give the desired compound (641 mg, 93%) as a colorless oil; $^1$H NMR (300 MHz, $CDCl_3$) δ7.23 (m, 4H), 5.5 (m, 0.25H, NH), 5.45–4.15 (series of m, 6H), 4.1–3.75 (series of m, 1H), 3.5–2.9 (series of m, 2H), 2.4–1.7 (m, 2H), 1.43 (s, 9H, t-Bu), 1.12–0.63 (m, 12H, 4×$CH_3$); $^{19}$F NMR δ−82.01 (s, $CF_3$), −120.5 to −123.6 (overlapping AB quartets, $CF_2$).

d) Preparation of N-L-valyl-N-[3,3,4,4,4-pentafluoro-1-(1-methylethyl)2-oxobutyl]-D,L-1,2,3,4-tetrahysro-3-isoquinolinamide, hydrochloride salt HCl gas was bubbled into a stirred solution of the product of example 15 (c) (641 mg, 1.11 mmol) in EtOAc (30 mL) at icebath temperature for 4 min. The reaction was then stirred at room temperature for 2 h, conc in vacuo and azeotroped with EtOAc to give the desired compound (385 mg, 68%) as a white foam.

e) Preparation of N-[4-(4-morpholinylcarbonyl)benzoyl]-L-valyl-N'-[3,3,4,4,4-pentafluoro-1-(1-methylethyl)2-oxobutyl]-D,L-1,2,3,4-tetrahydro-3-isoquinolinamide (MDL 104,339)

To a stirred suspension of 4-(4-morpholinylcarbonyl)benzoic acid (215 mg, 0.91 mmol) and benzyltriethylammonium chloride (4 mg, 0.008 mmol) in 1,2-dichloroethane (15 mL) was added thionyl chloride (0.07 mL, 0.91 mmol) and the reaction was heated to reflux. After 2 h, the reaction was allowed to cool to room temperature and concentrated in vacuo. The residue was then azeotroped with $CCl_4$ and placed under vacuum to give morpholinoterephthalic acid chloride (quantitative) as a light orange oil which was used without further purification. In a separate RB flask, a stirred solution of the product of example 15 (d) (385 mg, 0.749 mmol) in $CH_2Cl_2$ (15 mL) was cooled to −20° C. NMM (0.16 mL, 1.3 mmol) was added and immediately followed by the dropwise addition of the morpholinoterephthalic acid chloride in $CH_2Cl_2$ (5 mL) at such a rate as to maintain the internal reaction temperature at −10° C. or less. After the addition was complete, the reaction mixture was allowed to warm to room termperature. After 2 h at room temperature, the reaction mixture was diluted with CH$_2$Cl$_2$ (20 mL), washed with 1N HCl (2×20 mL), saturated NaHCO$_3$ (2×20 mL), brine (1×20 mL), dried (Na$_2$SO$_4$) and conc in vacuo to give a crude foam (410 mg). The crude white foam was immediately flash chromatographed (eluted with 1:27 MeOH—CH$_2$Cl$_2$) to give the desired product (MDL 104, 339)(95 mg, 18%) as a white foam; $^1$H NMR (300 MHz, CDCl$_3$) δ7.84 (m, 2H, aryl), 7.46 (m, 2H, aryl), 7.2 (m, 4H), 7.1 (m, 1H, NH), 6.83 (d, 0.5H, J=9 Hz, NH), 6.54 (d, 0.5H, J=9Hz, NH), 5.45–4.6 (series of m, 5H), 3.9–2.9 (series of m, 10H), 2.4–2.1 (pr of overlapping m, 2H), 1.2–0.65 (m, 12H, 4×CH$_3$); $^{19}$F NMR (CDCl$_3$) δ–82.13 (app t, CF$_3$), –121.3 and –123.1 (AB quartet J=296 Hz overlapping m, CF$_2$); MS (CI/CH$_4$) m/z 723, 695 (MH+), 578, 550, 549, 476, 379, 317, 289, 259, 234 (100), 220, 200.

EXAMPLE 16

Preparation of N-[4-(4-morpholinylcarbonyl) benzoyl]-L-valyl-N-[3,3,4,4,4-pentafluoro-1-(1-methylethyl)-2-oxobutyl]-L-1,2,3,4-tetrahydro-3-isoquinolinamide

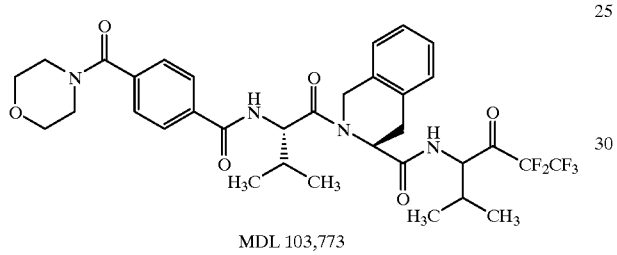

MDL 103,773 a) Preparation of N-[(1,1-dimethylethoxy)carbonyl]-L-valyl-L-1,2,3,4-tetrahydro-3-isoquinoline carboxylic acid The above-named compound was prepared from L-1,2,3,4-tetrahydro-3-isoquinoline carboxylic acid by the procedure described in example 15 (b). Said procedure yielded the desired compound (180 mg, 8.6%) as a white foam; $^1$H NMR (300 MHz, CDCl$_3$) δ8.32 (br s, 1H), 7.17 (m, 4H), 5.63 (d, 0.25H, J=8 Hz, NH), 5.5 (d, 0.75H, J=8 Hz, NH), 5.35 (m, 1H), 5.1–4.4 (series of m, 3H), 3.5–3.1 (series of m, 2H), 2.08 (m, 1H), 1.44 (s, 9H, tBu), 1.1–0.78 (m, 6H, 2×CH$_3$).

b) Preparation of N-[(1,1-dimethylethoxy) carbonyl]-L-valyl-N-[3,3,4,4,4-pentafluoro-1-(1-methylethyl)2-oxobutyl]-L-1,2,3,4-tetrahydro-3-isoquinolinamide The above-named compound was prepared from the product of example 16 (a) by the procedure described in example 15 (c). Said procedure yielded the desired compound (224 mg, 81%) as a yellow oil; $^1$H NMR (300 MHz, CDCl$_3$) δ7.2 (m, 4H), 5.4–4.6 (series of m, 6H), 4.1–3.7 (series of m, 1H), 3.5–2.9 (series of m, 2H), 2.4–1.8 (m, 2H), 1.44 (s, 9H, t-Bu), 1.15–0.7 (m, 12H, 4×CH$_3$).

c) Preparation of N-L-valyl-N-[3,3,4,4,4-pentafluoro-1-(1-methylethyl)-2-oxobutyl]-L-1,2,3,4-tetrahydro-3-isoquinolinamide, hydrochloride salt The above-named compound was prepared from the product of example 16 (b) by the procedure described in example 15 (d). Said procedure yielded the desired compound (141 mg, 71%) as a white foam; $^1$H NMR (300 MHz, CDCl$_3$) δ8.26 (br m, 2H), 7.18 (m, 4H), 5.5–4.5 (series of m, 6H), 4.1–3.7 (series of m, 1H), 3.5–2.8 (series of m, 2H), 2.3 (m, 1H), 1.9 (m, 1H), 1.2–0.7 (m, 12H, 4×CH$_3$); $^{19}$F NMR δ–82.0 (overlapping s, CF$_3$), –120.5 to –123.7 (overlapping AB quartets, CF$_2$).

d) Preparation N-[4-(4-morpholinylcarbonyl) benzoyl]-L-valyl-N-[3,3,4,4,4-pentafluoro-1-(1-methylethyl)-2-oxobutyl]-L-1,2,3,4-tetrahydro-3-isoquinolinamide (MDL 103,773)

The above-named compound was prepared from the product of example 16 (c) by the procedure described in example 15 (e). Said procedure yielded the desired compound (77 mg, 40%) as a white foam; $^1$H NMR (300 MHz, CDCl$_3$) δ7.87 (m, 2H, aryl), 7.47 (m, 2H, aryl), 7.22 (m, 4H), 7.06 (m, 1H, NH), 6.82 (d, 0.5H, J=9 Hz, NH), 6.54 (d, 0.5H, J=9 Hz, NH), 5.5–4.54 (series of m, 5H), 3.9–2.98 (series of m, 10H), 2.4–2.1 (pr of overlapping m, 2H), 1.2–0.65 (m, 12H, 4×CH$_3$); $^{19}$F NMR (CDCl$_3$) δ–82.13 (app t, CF$_3$), –121.3 and –123.1, –121.34 and –122.99 (overlapping AB quartets, J=296 Hz, CF$_2$); MS (CI/CH$_4$) m/z 723, 695 (MH+), 562, 550, 536, 522, 476, 393, 379, 363, 331, 317, 289, 262, 246, 234, 218, 206 (100), 186, 149, 139, 132. Anal. Calcd. for C$_{34}$H$_{39}$F$_5$N$_4$O$_6$: C, 58.78; H, 5.66; N, 8.07. Found: C, 58.17; H, 5.74; N, 7.44.

EXAMPLE 17

Preparation of N-[4-(4-morpholinylcarbonyl) benzoyl]-L-valyl-N-[3,3,4,4,4-pentafluoro-1-(1-methylethyl)-2-oxobutyl]-L-4-thiazolidamide

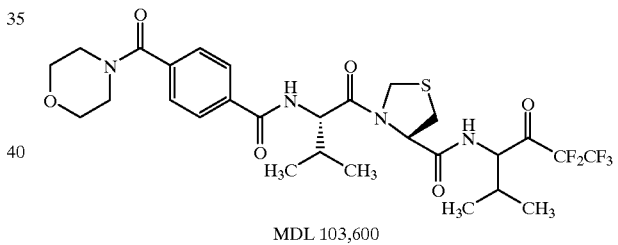

MDL 103,600 a) Preparation of N-[(1,1-dimethylethoxy)carbonyl]-L-valyl-L-thiazolidine-4-carboxylic acid To a stirred solution of L-thiazolidine-4-carboxylic acid (1.3 g, 10 mmol) and Et$_3$N (1.5 mL, 11 mmol) in DMF (30 mL) was added the product of example 15 (a) (2.8 g, 9.0 mmol) and the reaction was heated to 120° C. for 2.5 h. Upon cooling, the reaction was conc in vacuo and the oily residue was dissolved in EtOAc and washed with 1N HCl (2×30 mL), dried (MgSO$_4$) and conc. to give the desired compound (2.27 g, 68%) as a white foam; $^1$H NMR (300 MHz, CDCl$_3$) δ7.95 (br s, 1H), 5.57 (app t, 0.5H), 5.39 (d, 0.5H, J=9.5 Hz), 5.11 (t, 1H, J=5.6 Hz), 4.94 (d, 1H, J=8.6 Hz), 4.55 (d, 1H, J=8.3 Hz), 4.35 (m, 1H), 3.29 (d, 1H, J=5.6 Hz), 2.30–1.54 (series of m, 2H), 1.43 (s, 9H, tBu), 1.04–0.92 (m, 6H, 2×CH$_3$).

b) Preparation of N-[(1,1-dimethylethoxy) carbonyl]-L-valyl-N-[3,3,4,4,4-pentafluoro-1-(1-methylethyl)2-oxobutyl]-L-4-thiazolidamide To a stirred solution of the product of example 17 (a) (2.27 g, 6.8 mmol) and NMM (0.75 mL, 6.8 mmol) in dry CH$_2$Cl$_2$ (70 mL) at −20° C. under nitrogen was added dropwise isobutylchloroformate (0.89 mL, 6.8 mmol). After 20 min, 4-amino-1,1,1,2,2-pentafluoro-5-methyl-3-hexanone hydrochloride (1.72 g, 6.8 mmol) was added, immediately followed by another equivalent of NMM (0.75 mL, 6.8 mmol). The reaction mixture was stirred at −20° C. for 1 h, then poured into cold, dilute HCl and extracted with $CH_2Cl_2$. The organic extract was washed with water, dilute aqueous $NaHCO_3$, brine and dried ($MgSO_4$). Concentration in vacuo gave the desired compound (3.28 g, 92%) as a white foam; $^1$H NMR (300 MHz, $CDCl_3$) δ7.52 (br d, 1H, J=8 Hz, NH), 5.27 (m, 1H, NH), 5.00 (m, 2H), 4.51 (m, 1H), 4.38 (m, 1H), 3.64–3.38 (pr m, 1H), 3.12 (m, 1H), 2.40–1.84 (series of m, 3H), 1.44 (s, 9H, t-Bu), 1.15–0.84 (m, 12H, 4×$CH_3$).

c) Preparation of L-valyl-N-[3,3,4,4,4-pentafluoro-1-(1-methylethyl)-2-oxobutyl]-L-4-thiazolidamide, hydrochloride salt HCl gas was bubbled into a stirred solution of the product of example 17 (b) (3.2 g, 6.0 mmol) in EtOAc (50 mL) at icebath temperature for 4 min. The reaction was then stirred at room temperature for 2 h, conc in vacuo and azeotroped with EtOAc to give the desired compound (2.68 g, 96%) as a white foam; $^1$H NMR (300 MHz, $CDCl_3$) δ8.18 (m, 2H, $NH_2$), 5.36 (m, 1H), 2.39 (m, 3H), 1.30–0.84 (m, 12H, 4×$CH_3$); $^{19}$F NMR δ−82.0 (2s, ratio 1:3, $CF_3$), −120.0 and −123.8 (overlapping AB quartets, ratio 1:3, $CF_2$).

d) Preparation of N-[4-(4-morpholinylcarbonyl)benzoyl]-L-valyl-N-[3,3,4,4,4-pentafluoro-1-(1-methylethyl)-2-oxobutyl]-L-4-thiazolidamide (MDL 103,600)

To a stirred suspension of 4-(4-morpholinylcarbonyl)benzoic acid (1.20 g, 5.1 mmol) and benzyltriethylammonium chloride (8 mg, 0.016 mmol) in 1,2-dichloroethane (40 mL) was added thionyl chloride (0.37 mL, 5.1 mmol) and the reaction was heated at reflux. After 2.5 h, the reaction was allowed to cool to room temperature and concentrated in vacuo. The residue was then azeotroped with $CCl_4$ and placed under vacuum to give morpholinoterephthalic acid chloride (quantitative) as a light orange oil which was used without further purification. In a separate RB flask, a stirred solution of the product of example 17 (c) (2.0 g, 4.3 mmol) in $CH_2Cl_2$ (40 mL) was cooled to −20° C. NMM (0.93 mL, 8.6 mmol) was added and immediately followed by the dropwise addition of the morpholinoterephthalic acid chloride in $CH_2Cl_2$ (5 mL) at such a rate as to maintain the internal reaction temperature at −10° C. or less. After the addition was complete, the reaction mixture was allowed to warm to room termperature. After 1.5 h at room temperature, the reaction mixture was diluted with $CH_2Cl_2$ (20 mL), washed with 1N HCl (2×20 mL), saturated $NaHCO_3$ (2×20 mL), brine (1×20 mL), dried ($Na_2SO_4$) and conc in vacuo to give a foam which was immediately flash chromatographed (eluted with 1:27 MeOH—$CH_2Cl_2$) to give the desired product (MDL 103,600)(275 mg, 10%) as a white foam; $^1$H NMR (300 MHz, $CDCl_3$) δ7.85 (m, 2H, aryl), 7.49 (d, 2H, J=7.9 Hz, aryl), 7.04 (m, 1H, NH), 5.08 (m, 2H), 4.92 (m, 1H), 4.60 (pr d, 1H, J=9 Hz), 4.25 (br d, 0.5H, J=11 Hz), 3.88–3.30 (series of m, 7H), 3.14 (m, 1H), 2.34 (m, 1H), 2.22 (m, 1H), 1.92 (pr m, 1H), 1.64 (m, 1H), 1.32 (m, 1H), 1.05 (m, 9H, 3×$CH_3$), 0.87 (m, 3H, $CH_3$); $^{13}$C NMR δ172.1, 171.7, 169.3, 169.25, 169.20, 166.5, 156.6, 138.6, 134.97, 134.94, 127.4, 127.3, 127.2, 66.8, 62.5, 61.7, 59.5, 59.4, 58.7, 56.3, 56.2, 50.2, 49.9, 49.1, 48.17, 48.15, 48.12, 48.08, 48.05, 48.02, 47.9, 33.9, 33.8, 31.86, 31.81, 31.1, 30.9, 30.5, 29.1, 29.0, 25.6, 24.9, 20.0, 19.9, 19.7, 19.6, 19.5, 19.4, 19.0, 18.1, 17.8, 17.7, 16.3, 16.2, 16.1; $^{19}$F NMR ($CDCl_3$) δ−82.10 (s, $CF_3$), −121.22 and −122.88 (AB quartets J=296 Hz, $CF_2$); MS ($Cl/CH_4$) m/z (rel intensity) 679, 651 (MH+), 536, 416, 335, 317 (100), 225, 214.

The foregoing describes in detail the generic and specific aspects of the scope of the invention as well as the manner of making and using the invention. In addition thereto, although such procedures are known in the art, references setting forth state of the art procedures by which the compounds may be evaluated for their biochemical effects are also included herein.

By following the techniques referenced above, as well as by utilization of other known techniques, as well as by comparison with compounds known to be useful for treatment of the above-mentioned disease states, it is believed that adequate material is available to enable one of ordinary skill in the art to practice the invention. Of course, in the end-use application of the compounds of this invention, the compounds are preferably formulated into suitable pharmaceutical preparations such as tablets, capsules or elixers, for oral administration or in sterile solutions or suspensions for parenteral administration. The compounds of this invention can be administered to patients (animals and human) in need of such treatment in a dosage range of 5 to 500 mg per patient generally given several times, thus giving a total daily dose of from 5 to 2000 mg per day. As stated above, the dose will vary depending on severity of disease, weight of patient and other factors which a person skilled in the art will recognize.

Typically the compounds described above are formulated into pharmaceutical compositions as discussed below.

About 10 to 500 mg of a compound or mixture of compounds of formula 1 or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may he present as coatings or to otherwise modify the physical form of the dosage unit. For instance, tablets may be coated with shellac, sugar or both. A syrup or elixer may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. A compound of the formula

$$K-B-P_4-P_3-P_2-P_1-CF_2CF_3 \quad 1 \quad \text{(SEQ. ID NO. 1)}$$

wherein $P_1$ is Ala, bAla, Leu, Ile, Val, Nva, bVal, Met, Nle, or an N-methyl derivative;

$P_2$ is Ala, bAla, Leu, Ile, Val, Nva, bVal, Met, Nle, Gly, Phe, Tyr, Trp, or Nal(1) where the nitrogen of the alpha-amino group can be substituted with an R group where R is a $(C_{1-6})$alkyl, $(C_{3-12})$cycloalkyl, $(C_{3-12})$cycloalkyl$(C_{1-6})$alkyl, $(C_{4-11})$bicycloalkyl, $(C_{4-11})$bicycloalkyl$(C_{1-6})$alkyl, $(C_{6-10})$aryl, $(C_{6-10})$aryl$(C_{1-6})$alkyl, $(C_{3-7})$heterocycloalkyl, $(C_{3-7})$heterocycloalkyl$(C_{1-6})$alkyl, $(C_{5-9})$heteroaryl, $(C_{5-9})$heteroaryl$(C_{1-6})$alkyl, fused $(C_{6-10})$aryl$(C_{3-12})$cycloalkyl, fused $(C_{6-10})$aryl$(C_{3-12})$cycloalkyl$(C_{1-6})$alkyl, fused $(C_{5-9})$heteroaryl$(C_{3-12})$cycloalkyl, or fused $(C_{5-9})$heteroaryl$(C_{3-12})$cycloalkyl$(C_{1-6})$alkyl, or $P_2$ is Pro, 1,2,3,4-tetrahydro-3-isoquinoline carboxylic acid (Tic), thiazolidine-4-carboxylic acid (Tca), or Ind;

$P_3$ is Ala, bAla, Leu, Ile, Val, Nva, bVal, Met, or Nle or an N-methyl derivative, Pro, Ind, Tic or Tca, Lys or Orn each substituted on its omega amino group with a morpholino-B-group;

$P_4$ is Ala, bAla, Leu, Ile, Val, Nva, bVal, Met, or Nle or an N-methyl derivative or a bond;

B is a group of the formulae

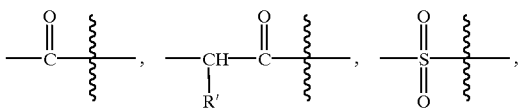

-continued

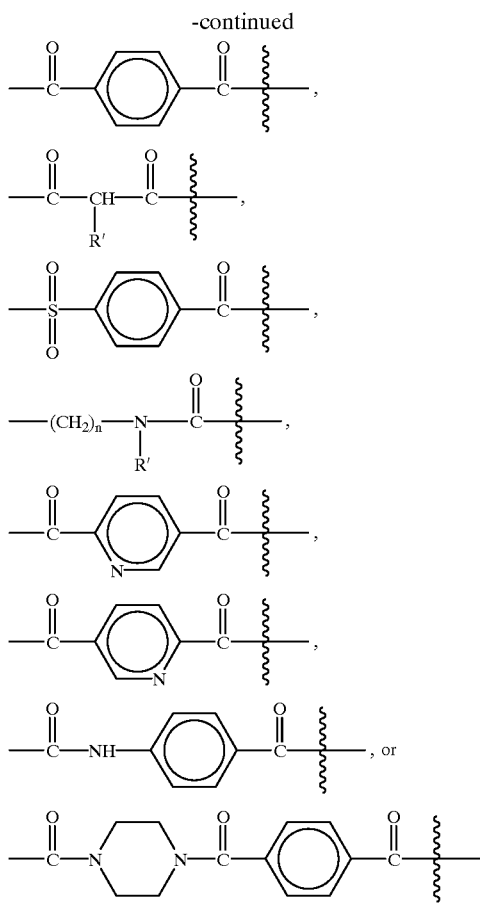

R' is a hydrogen or a $C_{1-6}$ branched or straight chain alkyl group;
n is zero or the integers 1 or 2;
K is

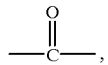; and

X is N or CH;
or a hydrate, isostere, or pharmaceutically acceptable salt thereof.

2. A compound of claim 1 wherein

B is a group of one of the formulae

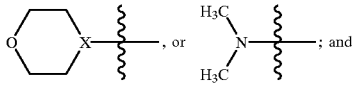

$P_1$ is Nva or Val;
$P_2$ is Pro;
$P_3$ is Ile, Val or Ala; and
$P_4$ is Ala or a bond.

3. A compound of claim 1 wherein
B is a group of one of the formulae

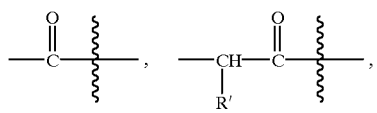

-continued

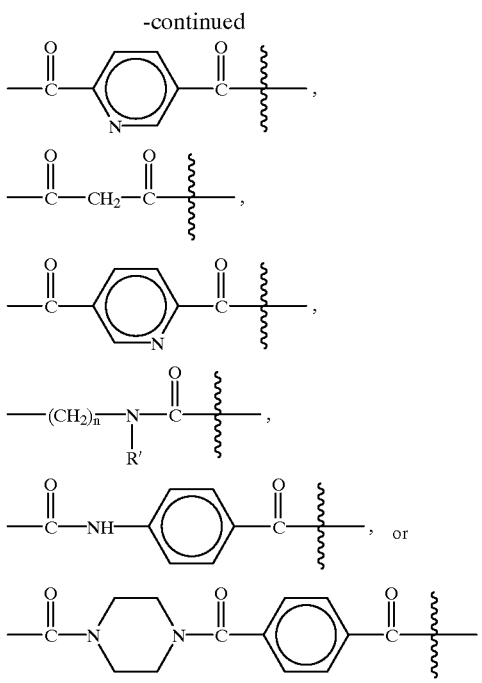

$P_1$ is Nva or Val;
$P_2$ is Pro, Tic, Tca;
$P_3$ is Ile, Val or Ala;
$P_4$ is Ala or a bond;
R' is a hydrogen or a $C_{1-6}$ branched or straight chain alkyl group; and
n is zero or the integers 1 or 2.

4. A compound of claim 1 wherein
B is a group of one of the formulae

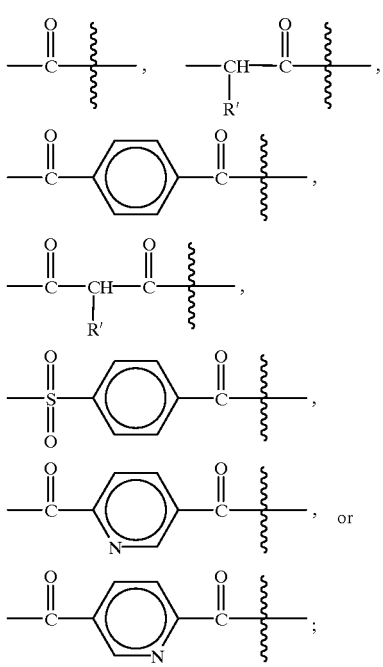

$P_1$ is Nva or Val;
$P_2$ is Gly where the nitrogen of the alpha-amino group is substituted with an R group where R is a $(C_{1-6})$ alkyl, $(C_{3-12})$cycloalkyl, cyclohexylmethyl, cyclopentylethyl, 2-bicyclo[1.1.0]-butyl, 2-bicyclo[2.2.1]hexyl, 1-bicyclo[2.2.2]octane, 2-bicyclohexylmethyl, phenyl, 1-naphthyl, 2-naphthyl, benzyl, phenethyl, 1-napthylmethyl, morpholinyl, piperidinyl, morpholinomethyl, pyridinyl, 2-quinoxalinyl, quinolinyl, 3-quinolinylmethyl, 2-indanyl or tetrahydroquinoline;

$P_3$ is Ile, Val or Ala;

$P_4$ is Ala or a bond;

R' is a hydrogen or a $C_{1-6}$ branched or straight chain alkyl group; and n is a zero or the integers 1 or 2.

5. A compound of claim 1 wherein said compound is N-[(Dimethylamino)carbonyl]-L-valyl-N-[3,3,4,4,4-pentafluoro-1-(1-methylethyl)-2-oxobutyl]-L-prolinamide.

6. A pharmaceutical composition comprising a compound of claim 1 and a pharmaceutically acceptable carrier.

7. A method of treating an inflammatory disease in a patient in need thereof which comprises administering to the patient an anti-inflammatory effective amount of a compound of claim 1.

8. A method of treating emphysema in a patient in need thereof which comprises administering to the patient an anti-inflammatory effective amount of a compound of claim 1.

* * * * *